(12) United States Patent
Faupel et al.

(10) Patent No.: US 6,577,391 B1
(45) Date of Patent: Jun. 10, 2003

(54) APPARATUS AND METHOD FOR DETERMINING TISSUE CHARACTERISTICS

(75) Inventors: Mark L. Faupel, Alphretta, GA (US); Shabbir B. Bambot, Suwanee, GA (US); Tim Harrell, Norcross, GA (US); J. David Farquhar, Commerce, GA (US); Glenn S. Arche, Duluth, GA (US); Walter R. Sanders, Duluth, GA (US); Edward L. Kimbrell, Buford, GA (US)

(73) Assignee: SpectRx, Inc., Norcross, GA (US)

( * ) Notice: Subject to any disclaimer, the term of this patent is extended or adjusted under 35 U.S.C. 154(b) by 0 days.

(21) Appl. No.: 09/533,817

(22) Filed: Mar. 24, 2000

Related U.S. Application Data

(63) Continuation-in-part of application No. PCT/US99/10947, filed on May 19, 1999.
(60) Provisional application No. 60/126,065, filed on Mar. 25, 1999.

(51) Int. Cl.[7] ............................. G01N 21/00; A61B 5/00
(52) U.S. Cl. ....................................... 356/337; 600/317
(58) Field of Search ........................ 356/337, 39, 300, 356/301, 302; 600/309, 310, 317

(56) References Cited

U.S. PATENT DOCUMENTS

| | | | |
|---|---|---|---|
| 4,213,462 A | * 7/1980 | Sato | 128/634 |
| 4,697,870 A | 10/1987 | Richards | |
| 4,731,326 A | 3/1988 | Thompson et al. | |
| 4,772,093 A | 9/1988 | Abele et al. | |
| 4,894,806 A | 1/1990 | Jen et al. | |
| 4,988,212 A | 1/1991 | Sun et al. | |
| 5,154,164 A | 10/1992 | Chikama | |
| 5,192,278 A | 3/1993 | Hayes et al. | |
| 5,201,908 A | 4/1993 | Jones | |
| 5,479,099 A | * 12/1995 | Jiles et al. | 324/235 |
| 5,489,536 A | 2/1996 | Ekechukwu | |
| 5,503,616 A | 4/1996 | Jones | |
| 5,536,235 A | 7/1996 | Yabe et al. | |
| 5,619,992 A | 4/1997 | Guthric et al. | |
| 5,674,182 A | 10/1997 | Suzuki et al. | |
| 5,699,795 A | 12/1997 | Richards-Kortum et al. | |
| 5,797,836 A | 8/1998 | Lucey et al. | |
| 5,827,177 A | 10/1998 | Oneda et al. | |
| 5,852,494 A | 12/1998 | Skladnev et al. | |
| 5,893,712 A | 4/1999 | Stone et al. | |
| 5,901,261 A | 5/1999 | Wach | |
| 5,902,246 A | 5/1999 | McHenry et al. | |
| 5,916,210 A | 6/1999 | Winston | |
| 5,941,834 A | 8/1999 | Skladnev et al. | |
| 5,953,477 A | 9/1999 | Wach et al. | |

* cited by examiner

Primary Examiner—Michael P. Stafira
(74) Attorney, Agent, or Firm—Fleshner & Kim, LLP

(57) ABSTRACT

An apparatus embodying the invention includes a probe head with an interrogation surface that is intended to be positioned adjacent or pushed into contact with a target material or tissue. The probe head is constructed to have a plurality of interrogation devices arranged across the face of the interrogation surface. The probe head is also constructed so that the interrogation device can conform to a non-uniform or non-planar surface of the target tissue. In some embodiments, the interrogation surface may have a particular shape that conforms to the shape of a target material. In other embodiments, one or more portions of the interrogation surface could be movable with respect to the remaining portions so that the interrogation surface could be movable with respect to remaining portions so that the interrogation surface can the thereby conform to a non-uniform surface. In still other embodiments, a plurality of separately moveable interrogation devices can be arranged across the interrogation surface. During a measurement process, the interrogation surface would be pressed into contact with the non-uniform surface to cause individual ones of the interrogation devices to move, thereby causing the probe head to conform to the non-uniform surface.

4 Claims, 19 Drawing Sheets

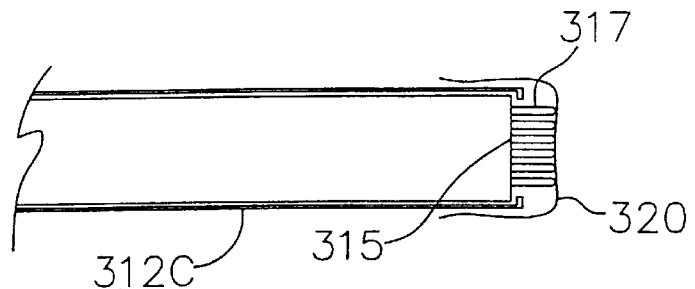
FIG. 15
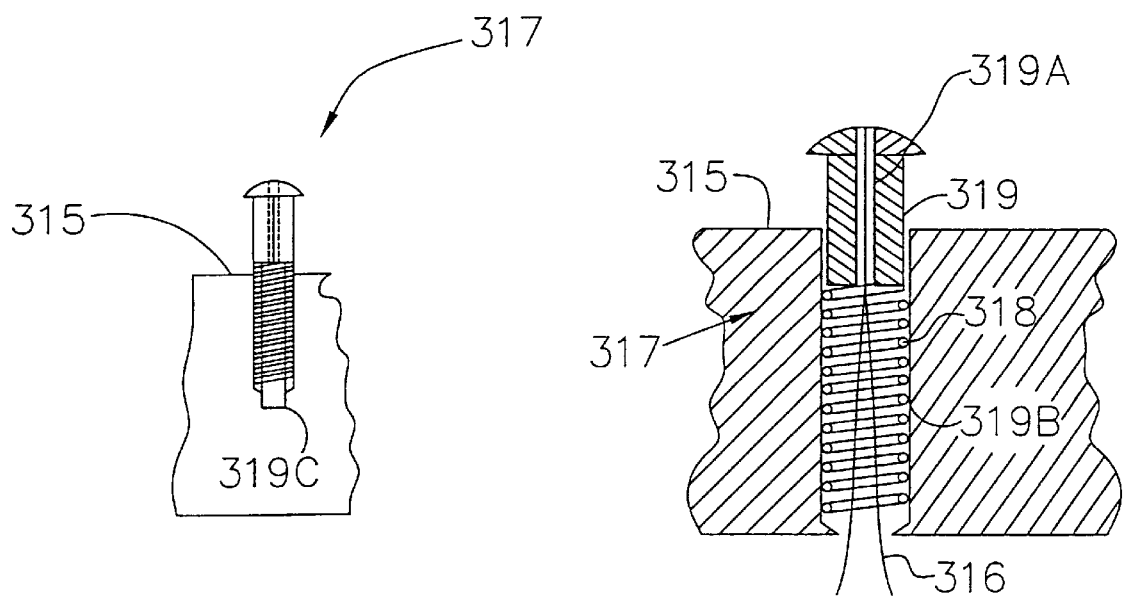
FIG. 16A
FIG. 16B

APPARATUS AND METHOD FOR DETERMINING TISSUE CHARACTERISTICS

RELATED APPLICATIONS

This application is a continuation-in-part of International Application No. PCT/US99/10947 filed May 19, 1999. This application also claims priority to Provisional Application No. 60/126,065 filed Mar. 25, 1999. The contents of the International Application and the Provisional Application are hereby incorporated by reference.

BACKGROUND OF THE INVENTION

1. Field of the Invention

The invention is related to apparatus and methods for determining characteristics of a target tissue of a patient.

2. Background of the Related Art

It is known to irradiate a target tissue with electromagnetic radiation and to detect returned electromagnetic radiation to determine characteristics of the target tissue. In known, methods, the amplitudes and wavelengths of the returned radiation are analyzed to determine characteristics of the target tissue. For instance, U.S. Pat. No. 4,718,417 to Kittrell et al. discloses a method for, diagnosing the type of tissue within an artery, wherein a catheter is inserted into an artery and excitation light at particular wavelengths is used to illuminate the interior wall of the artery. Material or tissue within the artery wall emits fluorescent radiation in response to the excitation light. A detector detects the fluorescent radiation and analyzes the amplitudes and wavelengths of the emitted fluorescent radiation to determine whether the illuminated portion of the artery wall is normal, or covered with plaque. The contents of U.S. Pat. No. 4,718,417 are hereby incorporated by reference.

U.S. Pat. No. 4,930,516 to Alfano et al. discloses a method for detecting cancerous tissue, wherein a tissue sample is illuminated with excitation light at a first wavelength, and fluorescent radiation emitted in response to the excitation light is detected. The wavelength and amplitude of the emitted fluorescent radiation are then examined to determine whether the tissue sample is cancerous or normal. Normal tissue will typically have amplitude peaks at certain known wavelengths, whereas cancerous tissue will have amplitude peaks at different wavelengths. Alternatively, the spectral amplitude of normal tissue will differ from cancerous tissue at the same wavelength. The disclosure of U.S. Pat. No. 4,930,516 is hereby incorporated by reference.

Still other patents, such as U.S. Pat. No. 5,369,496 to Alfano et al., disclose methods for determining characteristics of biological materials, wherein a target tissue is illuminated with light, and backscattered or reflected light is analyzed to determine the tissue characteristics. The contents of U.S. Pat. No. 5,369,496 are hereby incorporated by reference.

These methods rely on the information from steady state emissions to perform a diagnostic measurement. It is known that the accuracy of measurements made by these methods is limited by practical issues such as variation in lamp intensity and changes in fluorophore concentration. It is desirable to measure an intrinsic physical property to eliminate errors that can be caused by practical problems, to thereby make an absolute measurement with greater accuracy. One intrinsic physical property is the fluorescence lifetime or decay time of fluorophores being interrogated, the same fluorophores that serve as indicators of disease in tissue.

It is known to look at the decay time of fluorescent emissions to determine the type or condition of an illuminated tissue.

To date, apparatus for detection of the lifetime of fluorescent emissions have concentrated on directly measuring the lifetime of the fluorescent emissions. Typically, a very short burst of excitation light is directed at a target tissue, and fluorescent emissions from the target tissue are then sensed with a detector. The amplitude of the fluorescent emissions are recorded, over time, as the fluorescent emissions decay. The fluorescent emissions may be sensed at specific wavelengths, or over a range of wavelengths. The amplitude decay profile, as a function of time, is then examined to determine a property or condition of the target tissue. For instance, U.S. Pat. No. 5,562,100 to Kittrell et al. discloses a method of determining tissue characteristics that includes illuminating a target tissue with a short pulse of excitation radiation at a particular wavelength, and detecting fluorescent radiation emitted by the target tissue in response to the excitation radiation. In this method, the amplitude of the emitted radiation is recorded, over time, as the emission decays. The amplitude profile is then used to determine characteristics of the target tissue. Similarly, U.S. Pat. No. 5,467,767 to Alfano et al. also discloses a method of determining whether a tissue sample includes cancerous cells, wherein the amplitude decay profile of fluorescent emissions are examined. The contents of U.S. Pat. Nos. 5,562,100 and 5,467,767 are hereby incorporated by reference.

Unfortunately, these methods require expensive components that are capable of generating extremely short bursts of excitation light, and that are capable of recording the relatively faint fluorescent emissions that occur over time. The high cost of these components has prevented these techniques from being used in typical clinical settings. Other U.S. patents have explained that the decay time of fluorescent emissions can be indirectly measured utilizing phase shift or polar anisotropy measurements. For instance, U.S. Pat. No. 5,624,847 to Lakowicz et al. discloses a method for determining the presence or concentration of various substances using a phase shift method. U.S. Pat. No. 5,515,864 to Zuckerman discloses a method for measuring the concentration of oxygen in blood utilizing a polar anisotropy measurement technique. Each of these methods indirectly measure the lifetime of fluorescent emissions generated in response to excitation radiation. The contents of U.S. Pat. Nos. 5,624,847 and 5,515,864 are hereby incorporated by reference.

SUMMARY OF THE INVENTION

The invention encompasses apparatus and methods for determining characteristics of target tissues within or at the surface of a patient's body, wherein excitation electromagnetic radiation is used to illuminate a target tissue and electromagnetic radiation returned from the target tissue is analyzed to determine the characteristics of the target tissue. Some apparatus and methods embodying the invention can be used to perform a diagnosis at or slightly below the surface of a patient's tissues. For instance, methods and apparatus embodying the invention could be used to diagnose the condition of a patient's skin, the lining of natural body lumens such as the gastrointestinal tract, or the surfaces of body organs or blood vessels. Embodiments of the invention are particularly well suited to analyzing epithelial tissue. Other apparatus and methods embodying the invention can be used to perform a diagnosis deep within a patient's body tissues where the excitation radiation has to pass through several centimeters of tissue before it interacts with the target tissue, such as in diagnosis of tumors and lesions deep in a patient's breast.

The returned electromagnetic radiation can comprise electromagnetic radiation that is scattered or reflected from or transmitted through the target tissue. Analysis of the scattered, reflected or transmitted excitation radiation gives a measure of absorption and scattering characteristics of the target tissue. This information can be used by itself to provide a diagnosis, or the information can be used in conjunction with the results of fluorescent emission measurements, as discussed below, to arrive at a more accurate measurement. The reflected or scattered excitation radiation can be measured using intensity based techniques, phase shift techniques, or polarization anisotropy based techniques. While polarization preserving fiber optics are not currently available, should they be developed in the future, polar anisotropic techniques could also be used.

The returned electromagnetic radiation can also comprise only fluorescent emissions from the target tissue that are caused by the excitation electromagnetic radiation. In this instance, apparatus or methods embodying the invention would measure the lifetime or decay time of the fluorescent emissions and use this information to determine characteristics of the target tissue. The fluorescent emissions may be generated by endogenous or exogenous fluorescent materials in the target tissue. Both phase shift and polar anisotropy techniques could be used to perform these types of measurements.

A device or method embodying the invention can be used to determine the conditions of multiple portions of a target tissue, and the determined conditions can be used to create a map of the target tissue. Such a map could then be either displayed on a display screen, or presented in hard copy format.

An instrument embodying present invention could be in the form of an endoscope designed to be introduced into a natural lumen or a cavity of a patient's body. Alternatively, the instrument might be in the form of a catheter designed to be introduced into blood vessels of a patient's body. Regardless of whether the apparatus is in the form of an endoscope or a catheter, the apparatus could include means for delivering a therapeutic pulse of electromagnetic radiation to the target tissue. The device could also include means for delivering a therapeutic dose of medication to the target tissue. Further, the instrument could include means for sampling the target tissue depending upon the determined condition of the target tissue.

An apparatus embodying the invention that is well suited to developing a map of target tissue conditions may include a plurality of optical fibers that are arranged in a predetermined pattern on the face of a test instrument. Each optical fiber would be capable of delivering excitation radiation and conducting return radiation to a detector. Alternatively, each detection position on the face of the instrument could include at least one optical fiber for delivering excitation radiation and at least one separate fiber for receiving returned radiation. In yet other alternatives, multiple fibers could be used at each position for the excitation or return radiation, or both. By pressing the face of the instrument against the target tissue, multiple measurements can be taken at multiple positions simultaneously.

An apparatus as described above could also be configured so that once a first set of measurements are taken with the instrument, the locations of the optical fibers could be moved incrementally, and a second set of measurements could be recorded. This could be done by repositioning the instrument face, or by keeping the instrument face stationary, and repositioning the optical fibers behind the instrument face. This process could be repeated several times to obtain multiple sets of readings from the target tissue. The additional sets of measurements could be taken on the same area as the first set, or at different locations on the target tissue.

An instrument as described above could be configured to allow rotation of the optical fibers between a plurality of predetermined rotational positions. One embodiment could be configured so that the optical fibers are located at a series of unique positions as the optical fibers are rotated between the predetermined rotational positions. This would allow the device to capture multiple readings at a large number of unique positions on the target tissue. Such a multiple cycle measurement process would allow the optical fibers to be spaced far enough apart to reduce or eliminate cross-talk, while still providing greater resolution than would be possible with a single measurement cycle.

An instrument for determining characteristics of a target material according to the invention could include a probe face configured to conform to a non-uniform and/or non-planar surface area of a target material. According to one embodiment, the probe face could be shaped to conform to a non-uniform surface area of a target material. For example, the probe body could be a fused glass cane, where one end of the fused cane is shaped to conform to a non-uniform surface area of a target material. Further, the probe body could be attached to a flexible bundle of optic fibers. The instrument could comprise an outer housing, an inner core and a probe face attached to the inner core and comprising a plurality of interrogation devices arranged in a predetermined pattern.

According to another embodiment, of the invention, the instrument could include an inner core that is rotatably mounted within the housing, where the probe face is mounted on the inner core. The inner core could comprise a first inner core and a second inner core. The second inner core would preferably be configured to slide axially inside the first inner core and rotate with the first inner core when the first inner core is rotated. The probe face would preferably comprise first and second probe faces. The first probe face would preferably be attached to the first inner core and have a centrally located opening for allowing the second inner core to axially slide with respect to the first inner core such that the second probe face is not located in the same plane as the first probe face.

According to another embodiment of the invention, a plurality of interrogation devices may be spring-loaded in the probe face so that the plurality of interrogation devices collectively conform to a non-uniform surface area of a target material. Preferably, each of the plurality of interrogation devices comprises a hollow shaft within which the respective interrogation device is axially movably disposed, the hollow shaft being positioned in the probe face. A spring disposed within the hollow shaft would allow the interrogation device to move axially within the hollow shaft to allow the interrogation devices to collectively conform to a non-uniform surface area of a target material. The plurality of interrogation devices may comprise a plurality of optical fibers.

In some embodiments, the device could include a detector array, such as a CCD. Light scattered from or generated by a target material could be conducted to the detector array by at least some of the optical fibers.

Any of the above discussed instruments may include a flexible sheath configured to cover and conform to the shape of the probe face. The flexible sheath is preferably optically clear, optically uniform, disposable, and formed of a material having a low durometer and high tear strength. Further, an index matching agent may be located between the flexible sheath and the plurality of interrogation devices.

A method of detecting characteristics of a target material according to the invention preferably comprises positioning a plurality of interrogation devices that are arranged in a pattern adjacent a first plurality of interrogation positions on a non-uniform surface area of a target material so that the plurality of interrogation devices conform to the non-uniform surface area, and detecting characteristics of the target material at the first plurality of interrogation positions.

The method may further comprise repositioning the plurality of interrogation devices so that they are adjacent at least one additional plurality of interrogation positions on the target material, and detecting characteristics of the target material at the at least one additional plurality of interrogation positions. Preferably, the first and at least one additional plurality of positions are not coincident. The repositioning step may comprise rotating the plurality of interrogation devices around a common axis. The method could further include steps of withdrawing the probe from the target material before conducting the rotation step, and then advancing the probe back into contact with the target material after the rotation has been accomplished.

Each detecting step may comprise detecting a first type of characteristics of the target material at a plurality of interrogation positions, and detecting a second type of characteristics of the target material at the same plurality of interrogation positions. The first type of characteristics may comprise scattering characteristics, and the second type of characteristics may comprise fluorescent characteristics.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Preferred embodiments of the present invention will now be described with reference to the following drawing figures, wherein like elements are referred to with like reference numerals, and wherein:

FIG. 15 is a partial side view of the fiber optic head of the device of FIG. 11;

FIG. 16A is a partial side view of the probe face of the device of FIG. 11;

FIG. 16B shows an individual spring-loaded optic fiber according to the invention;

DETAILED DESCRIPTION OF PREFERRED EMBODIMENTS

Figure 1:
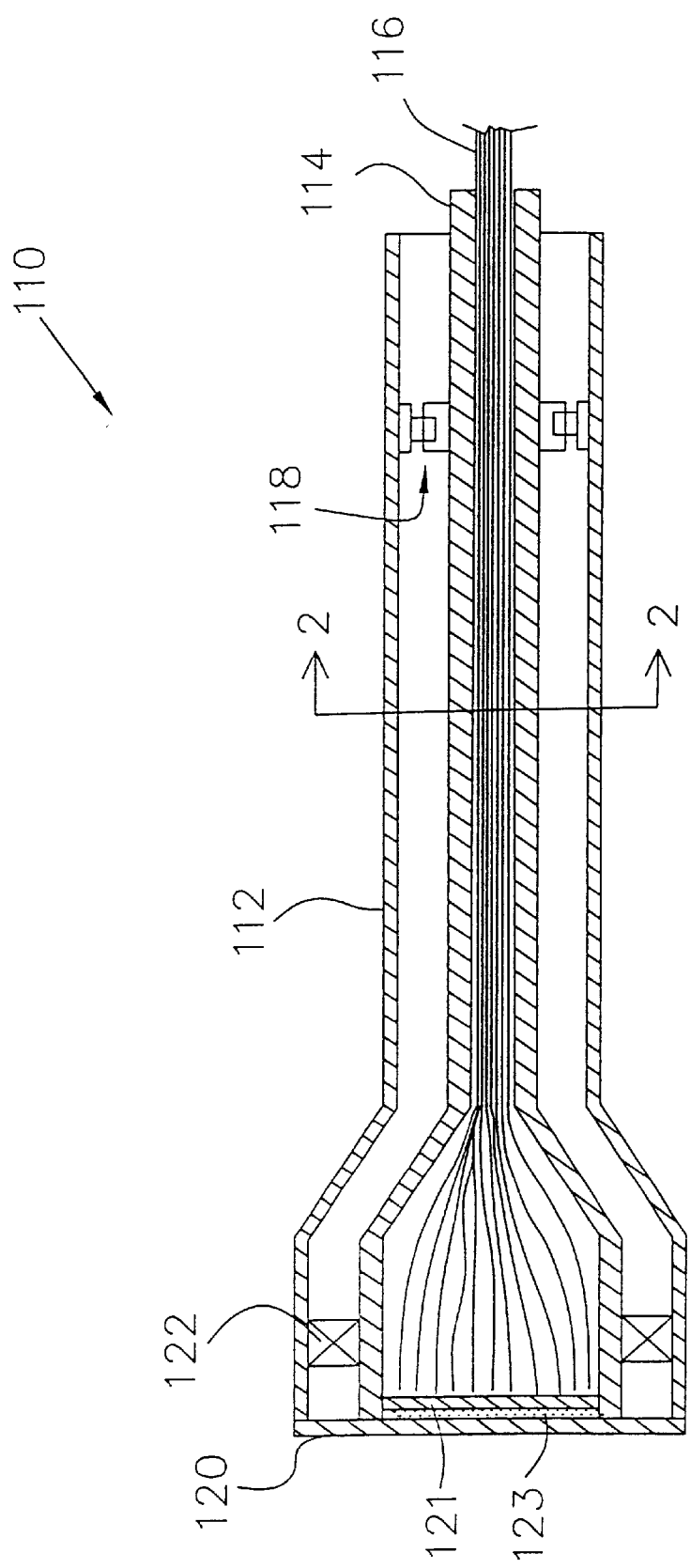
FIG. 1 is a cross-sectional view of a device embodying the invention.

The invention is primarily concerned with devices which are used to take measurements on a target material or tissue. Devices embodying the invention are capable of conforming to nonplaner tissue so that accurate spectroscopic based measurements can be taken.

Devices and method embodying the invention can utilize a wide range of different spectroscopic interrogation techniques to detect or diagnose the condition of a target material or tissue. For instance, a device embodying the invention could be configured to take reflectance or scattering measurements, or measurements of fluorescence produced by a target material or tissue. The fluorescence measurements could include measurements of the amplitude of particular wavelengths, or measurements of the lifetime of a fluorescent emission. Furthermore, a scattering measurement, or a fluorescence measurement, could be conducted using phase shift or a polarization anisotropic method. Some of the many different types of spectroscopic interrogation techniques which could be utilized in the device or method embodying the invention are described in the background section above.

In devices and methods embodying the invention, an interrogation device, such as a probe, would be brought into contact with, or closely adjacent to a target material or tissue. The probe face in contact with the target material or tissue would extend across an area of the target material or tissue to be interrogated. Multiple measurements would be made at a plurality of different locations on the area contacted by the probe face. Ideally, the plurality of measurements would be made substantially simultaneously at all the plurality of interrogation points on the target material or tissue.

In preferred embodiments of the invention, excitation electromagnetic radiation would be delivered to a plurality of different locations on a target material or tissue using a plurality of optical fibers. The electromagnetic radiation could be in the visible light range, or in the infrared or ultraviolet light ranges. For purposes of the following description, the term "light" will be used to refer to any wavelength of electromagnetic radiation that is delivered to target material or tissue for purposes of conducting a spectroscopic measurement.

A device and method embodying the invention could then include collecting light that is scattered or reflected from the target material or tissue at each of the plurality of interrogation points. The light could be collected using a plurality of optical fibers. In addition, a device or method embodying the invention could collect fluorescent light, which is produced by the target material or tissue in response to the excitation light. As mentioned above, a variety of different types of spectroscopic analyses could be performed using the collected scattered or fluorescent light.

The inventors contemplate that a device embodying the invention could be used to conduct measurements on many different types of materials. A device embodying the invention could also be utilized to determine the status or condition of a target tissue on a human or animal patient. A probe embodying the invention could be configured to contact the skin of a patient or a device could be configured to contact a target tissue area inside the body of a patient. In this regard, endoscopes, catheters, and other probing devices embodying the invention could be used to bring an interrogating probe face into contact with a target tissue inside the body of a patient.

One of the most difficult problems with in vivo tissue diagnostics and disease measurement is the biological diversity of normal tissue properties between different patients, or even within the same patient. Furthermore, this diversity is time variant both in the long term and in the short term. Long term variations may be due to patient age, hormonal milieu, metabolism, mucosal viscosity, and circulatory and nervous system differences. Short term variations may be from blood perfusion changes due to heart beat, physical movement, local temperature changes, etc.

Because of the variability of tissue characteristics, to accurately determine whether a target tissue is diseased, it is helpful to compare measurements of a suspect target tissue to measurements of normal tissues from the same patient. If possible, the measurements of the known normal tissue, should be made concurrently or simultaneously with the measurements of the suspect target tissue. The normal tissue measurements then serve as a baseline for normalcy, variations from which may be interpreted as disease. To arrive at a baseline measurement, a number of strategies can be used.

First, visual characteristics such as pigmentations (nevi) in skin, or polyps in the colon, can be used to identify potentially abnormal regions. Normalized or averaged spectra of multiple regions surrounding these potentially abnormal, visually distinct regions can be used to establish baseline measurements. The baseline measurements can then be compared to measurements taken on the abnormal, visually distinct regions. Measurements of normal and abnormal regions based on visual characteristics could be automated using imaging capabilities of the measurement device itself.

In an alternate strategy, measurements can be taken on spaced apart regions along a portion of a lumen or tissue. The spacing between the regions would be dependent on the type of tissue being diagnosed. Then, differentials between individual measurements taken at different regions would be calculated. If a differential for one area of a target tissue, relative to the surrounding tissue, exceeds a preset amount, the tissue area would be diagnosed as diseased.

In yet another alternate strategy, a gradient in spectral response as one moves away from a visually suspicious site could also be used as a marker for disease. This is easily automated and can be implemented effectively in any imaging modality.

In addition, pattern recognition algorithms is (e.g., neural nets) could also be used to analyze differences in readings taken from various sites in the same patient or from multiple readings from different patients.

A first device embodying the invention that can be used to determine tissue characteristics is shown, in longitudinal cross-section, in FIG. 1. The instrument 110 includes a cylindrical outer housing 112 with a circular end cap 120 configured to abut the target tissue. A rotating cylindrical inner core 114 is mounted in the outer housing 112. A bundle of optical fibers 116 are located inside the inner core 114.

The optical fibers 116 pass down the length of the inner core 114 and are arranged in a specific pattern at the end adjacent the end cap 120 of the outer housing 112. The end of the inner core 114 adjacent the end cap 120 is mounted within the outer housing 112 with a rotating bearing 122. The end cap 120 is at least partially transparent or transmissive so that electromagnetic radiation can pass from the optical fibers, through the end cap, to illuminate a target tissue adjacent the end cap 120. Light scattered from or generated by the target tissue would then pass back through the end cap 120 and back down the optical fibers 116.

The inner core 114 is also mounted inside the outer housing 112 by a detent mechanism 118. The detent mechanism is intended to support the inner core 114, and ensure that the inner core is rotatable within the outer housing 112 by predetermined angular amounts.

Figure 2A:
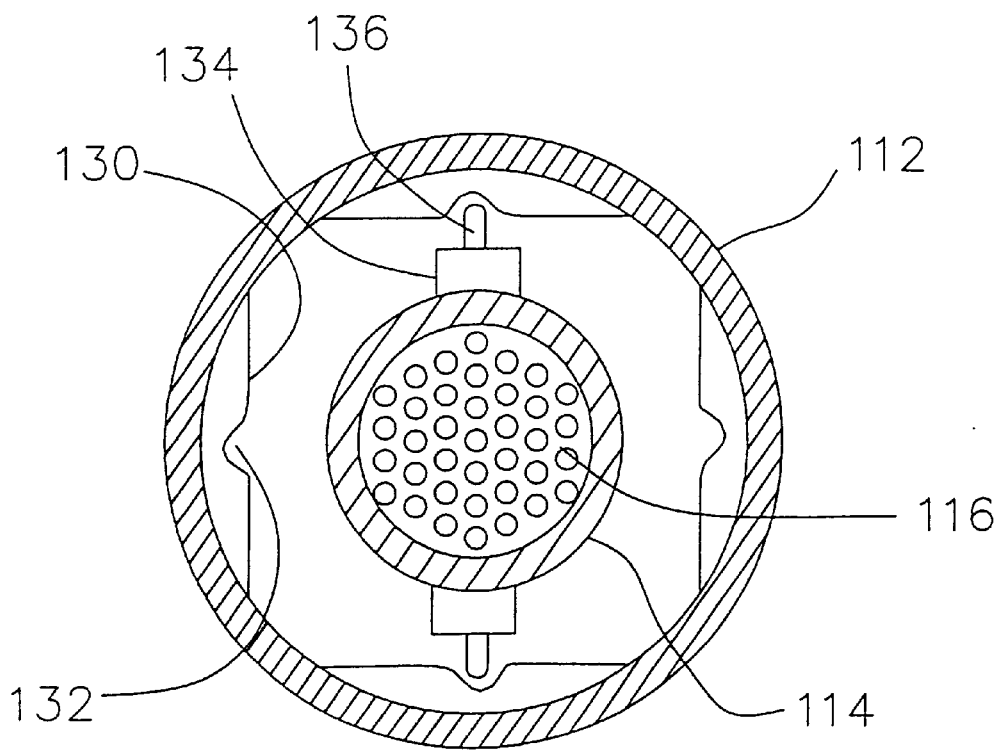
FIGS. 2A and 2B are cross sectional views of the device shown in FIG. 1 taken along section line 2—2.

A cross sectional view of the instrument shown in FIG. 1, taken along section line 2—2 of FIG. 1, is shown in FIG. 2A. The inner core 114 is supported within the outer housing 112 by the detent mechanism. In this embodiment, the detent mechanism includes two mounts 134 with spring loaded fingers 136 that are biased away from the inner core 114. The detent mechanism also includes four stoppers 130, each of which has a central depression 132. The spring loaded fingers 136 are configured to engage the central depressions 132 of the stoppers 130 to cause the rotatable inner core to come to rest at predetermined angular rotational positions. In the embodiment shown in FIG. 2A, four stoppers are provided in the inner surface of the outer housing 112. Thus, the inner core 114 will be rotatable in increments of 90°. In alternate embodiments similar to the one shown in FIG. 2A, four mounts 134, each having its own spring loaded finger 136, could be attached to the inner core 114. The provision of four such mounts would serve to keep the inner core 114 better centered inside the outer housing 112.

Figure 2B:
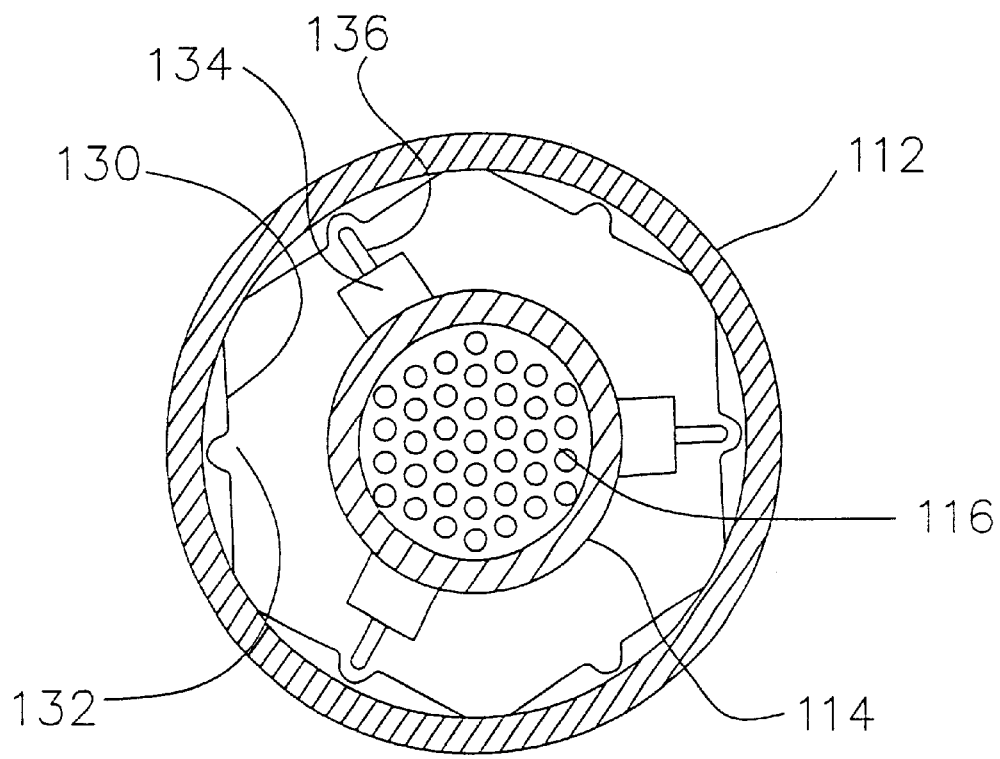

An alternate embodiment of the detent mechanism is shown in FIG. 2B. In this embodiment, six stoppers 130 are spaced around the inside of the outer housing 112. Three mounts 134, each having its own spring loaded finger 136, are mounted on the inner core 114. The three mounts 134 are spaced around the exterior of the inner core 114 approximately 120° apart. This embodiment will allow the inner core to be rotated to predetermined positions in increments of 60°. In addition, the location of the three mounts, 120° apart, helps to keep the inner core 114 supported in the center of the outer housing 112.

The ends of the optical fibers may be mounted on a circular end plate 121 that holds the optical fibers in a predetermined pattern. The circular end plate 121 would be rigidly attached to the end of the cylindrical inner core 114. In addition, an index matching agent 123 may be located between the end plate 121 and the end cap 120 on the outer housing 112. The index matching agent 123 can serve as both an optical index matching agent, and as a lubricant to allow free rotation of the end plate 121 relative to the end cap 120.

Figure 3:
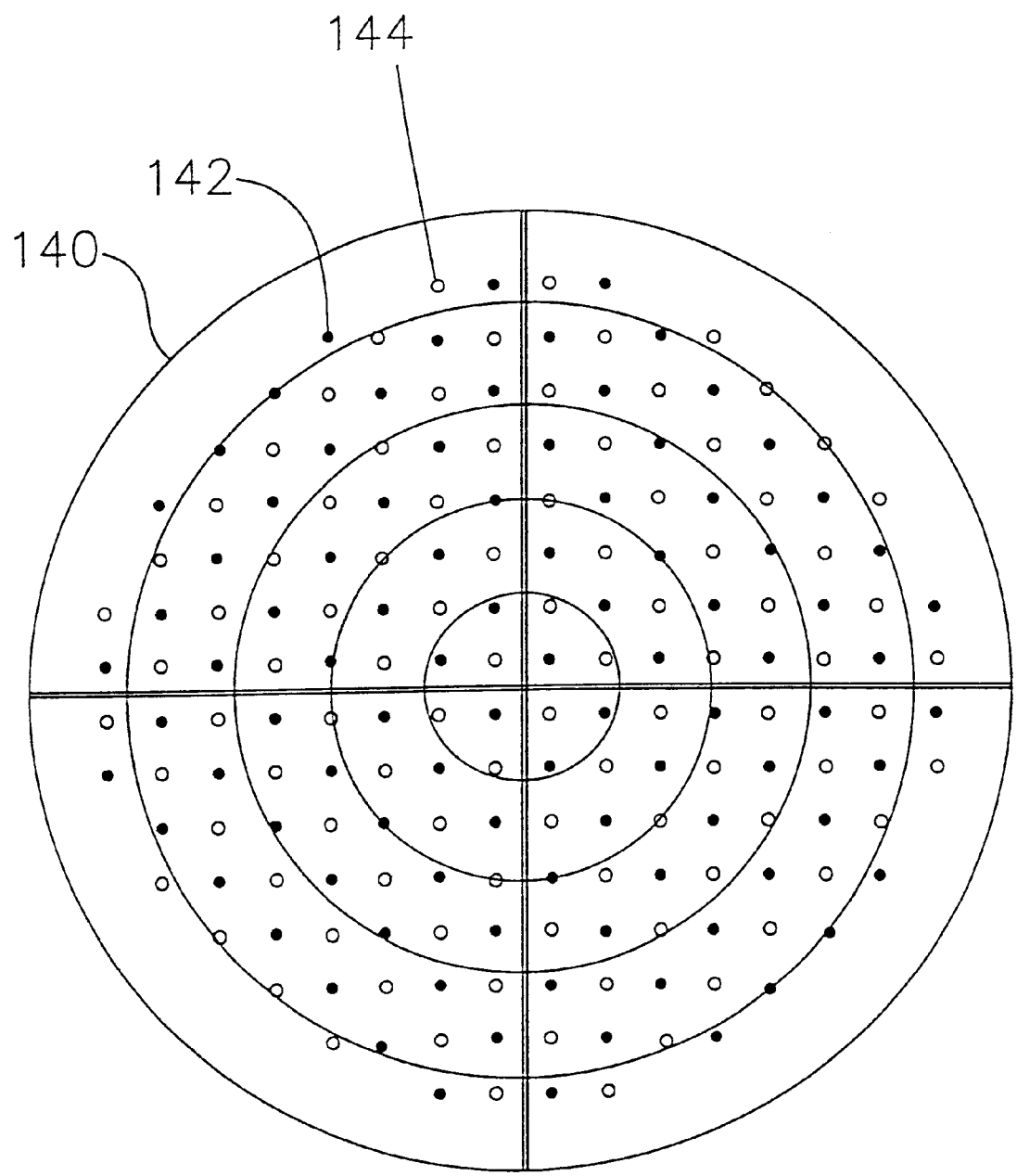
FIG. 3 is a diagram showing the, pattern of interrogation points of a device embodying the invention.

A diagram showing how the optical fibers are positioned on the face of an embodiment of the instrument is shown in FIG. 3. The face of the instrument, which would be the end cap 120 of the device shown in FIG. 1, is indicated by reference number 140 in FIG. 3. The black circles 142 represent the locations of optical fibers behind the end cap 120. The hollow circles 144 represent the positions that the optical fibers will move to if the inner core 114 of the instrument is rotated 90°. Thus, each of the circles represent positions that can be interrogated with the optical fibers.

In some embodiments of the device, a single optical fiber will be located at each of the positions shown by the black circles 142 in FIG. 3. In this instance, excitation light would travel down the fiber and be emitted at each interrogation position indicated by a black circle 142. Light scattered from or produced by the target tissue would travel back up the same fibers to a detector or detector array. In alternate embodiments, pairs of optical fibers could be located at each position indicated by a black circle 142. In the alternate embodiments, one optical fiber of each pair would conduct excitation light to the target tissue, and the second optical fiber of each pair would conduct light scattered from or generated by the target tissue to a detector. In still other alternate embodiments, multiple fibers for carrying excitation light and/or multiple fibers for carrying light scattered from or generated by the target tissue could be located at each interrogation position indicated by a black circle 142.

To use an instrument having the optical fiber pattern shown in FIG. 3, the instrument would first be positioned so that the end cap 120 is adjacent the target tissue. The end cap 120 may be in contact with the target tissue, or it might be spaced from the surface of the target tissue. Also, an index matching material may be interposed between the end cap and that target tissue. Then, the optical fibers would be used during a first measurement cycle to simultaneously measure tissue characteristics at each of the interrogation positions in FIG. 3 having a black circle 142. The tissue characteristics could be measured using any of the measurement techniques discussed above. Then, the inner core 114 would be rotated 90° within the outer housing 112, and the optical fibers would be used during a second measurement cycle to simultaneously measure tissue characteristics at each of the interrogation positions in FIG. 3 having a hollow circle 144.

Constructing an instrument as shown in FIGS. 1, 2A or 2B, and having the optical fiber pattern shown in FIG. 3, has several important advantages. First, constructing an instrument in this manner allows the instrument to interrogate many more points in the target tissue than would have been possible if the inner core did not rotate. The ability to rotate the inner core 114, and take a second series of measurements at different locations on the target tissue essentially increases the resolution of the device. In addition, when a large number of optical fibers are packed into the tissue contacting face of an instrument, cross-talk between the optical fibers can occur. The cross-talk can occur when excitation light from one interrogation position scatters from the target tissue and enters an adjacent interrogation position. Cross-talk can also occur if excitation light from a first interrogation position travels through the target tissue and enters an adjacent interrogation position. One of the easiest ways to reduce or eliminate cross-talk is to space the interrogation positions farther apart. However, increasing the spacing between interrogation positions will reduce the resolution of the device.

An instrument embodying the present invention, with a rotatable inner core, allows the interrogation positions to be spaced far enough apart to reduce or substantially eliminate cross-talk, while still obtaining excellent resolution. Thus, good resolution is obtained without the negative impact to sensitivity or selectivity caused by cross-talk. In addition, fewer optical fibers and fewer corresponding detectors ,are required to obtain a given resolution.

In addition, the ability to obtain a plurality of tissue measurements simultaneously from positions spaced across the entire target tissue has other benefits. If the instrument is intended to detect cancerous growths or other tissue maladies, the target tissue area interrogated by the instrument is likely to have both normal tissue, and diseased tissue. As noted above, tissue characteristics can vary significantly from person to person, and the tissue characteristics can vary significantly over relatively short periods of time. For these reasons, the most effective way to determine the locations of diseased areas is to establish a baseline for normal tissue, then compare the measurement results for each interrogation point to the baseline measurement. In other words, the easiest way to determine the location of a diseased area is to simply look for a measurement aberration or variance.

Because tissue characteristics can change relatively quickly, in order to establish accurate, clearly defined variances between tissue characteristics, it is desirable to take a plurality of readings simultaneously over as large an area as possible. Ideally, all measurements should be conducted during the same time period. Because tissue tumors can be as small as approximately 1 mm, the resolution of the device is preferably approximately 1 mm, or less. In other words, to obtain the requisite resolution, the spacing between interrogation positions should be approximately 1 mm, or less. Unfortunately, when the interrogation positions are approximately 1 mm apart, significant cross-talk can occur, and the accuracy of the measurement results is poor.

An instrument embodying the present invention allows the interrogation positions to be spaced sufficiently far apart to essentially eliminate cross-talk, while still obtaining the requisite approximately 1 mm resolution. Although not all measurements are obtained at exactly the same time, during each measurement cycle, simultaneous measurements are made at positions spaced across the entire target tissue, which should include both normal and diseased areas. Thus, the results from each measurement cycle can be used to detect variances in tissue characteristics that help to localize diseased areas. For these reasons, an instrument embodying the present invention balances the competing design requirements of resolution, elimination of cross-talk, and the desire to make all measurements simultaneously to ensure that time-varying tissue characteristics are taken into account.

Figure 4:
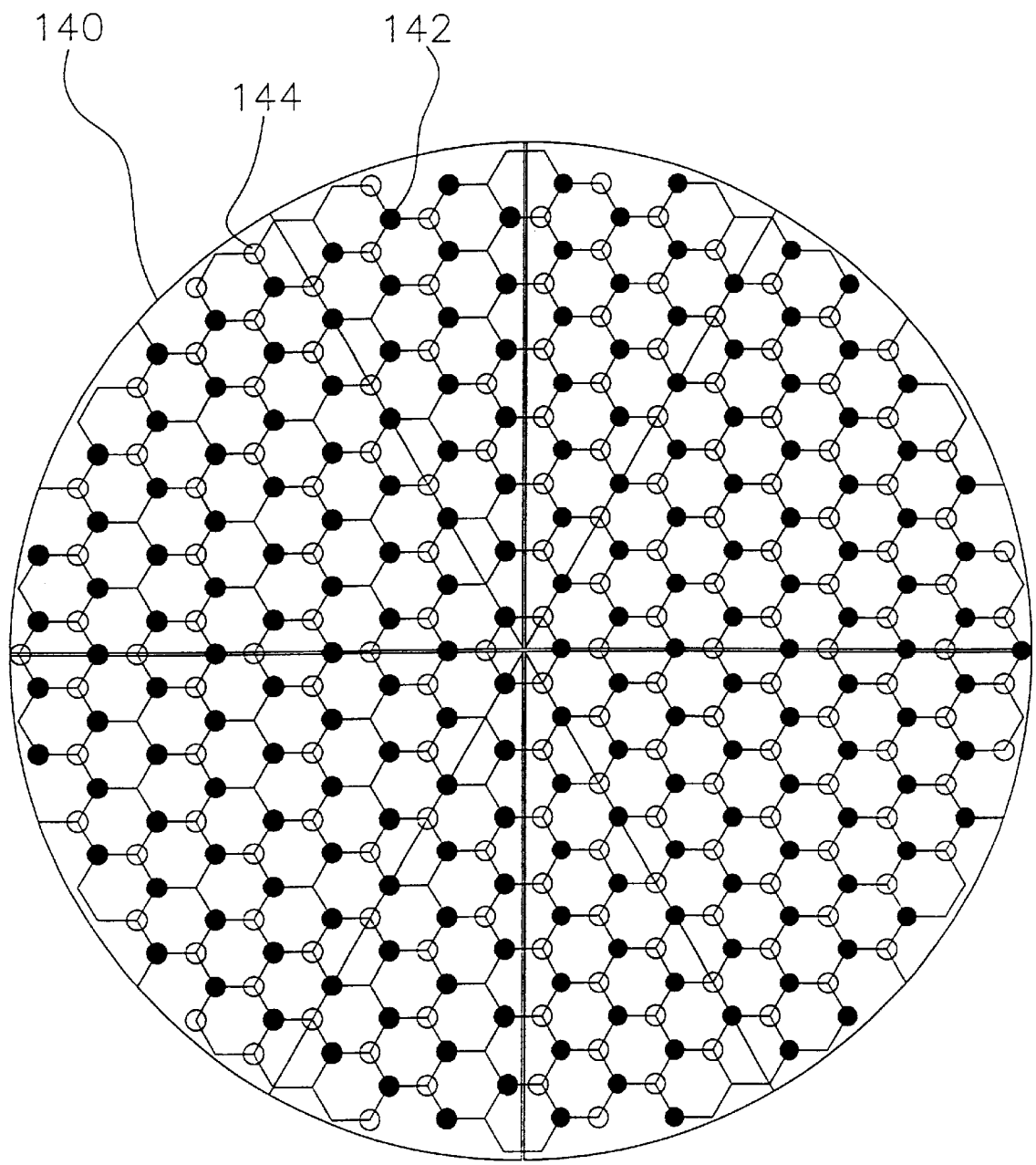
FIG. 4 is another diagram showing the pattern of interrogation points of a device embodying the invention.

A second arrangement for the optical fibers of a device as shown in FIG. 1 is depicted in FIG. 4. In this embodiment, the interrogation positions are arranged in a hexagonal honeycomb pattern. The black circles 142 indicate the positions that would be occupied by optical fibers during a first measurement cycle, and the hollow circles 144 indicate positions that would be occupied by the optical fibers during a second measurement cycle after the inner core 112 has been rotated by 60°. This pattern achieves maximum spacing between adjacent interrogation positions during each measurement cycle, and essentially doubles the resolution of the instrument.

Figure 5:
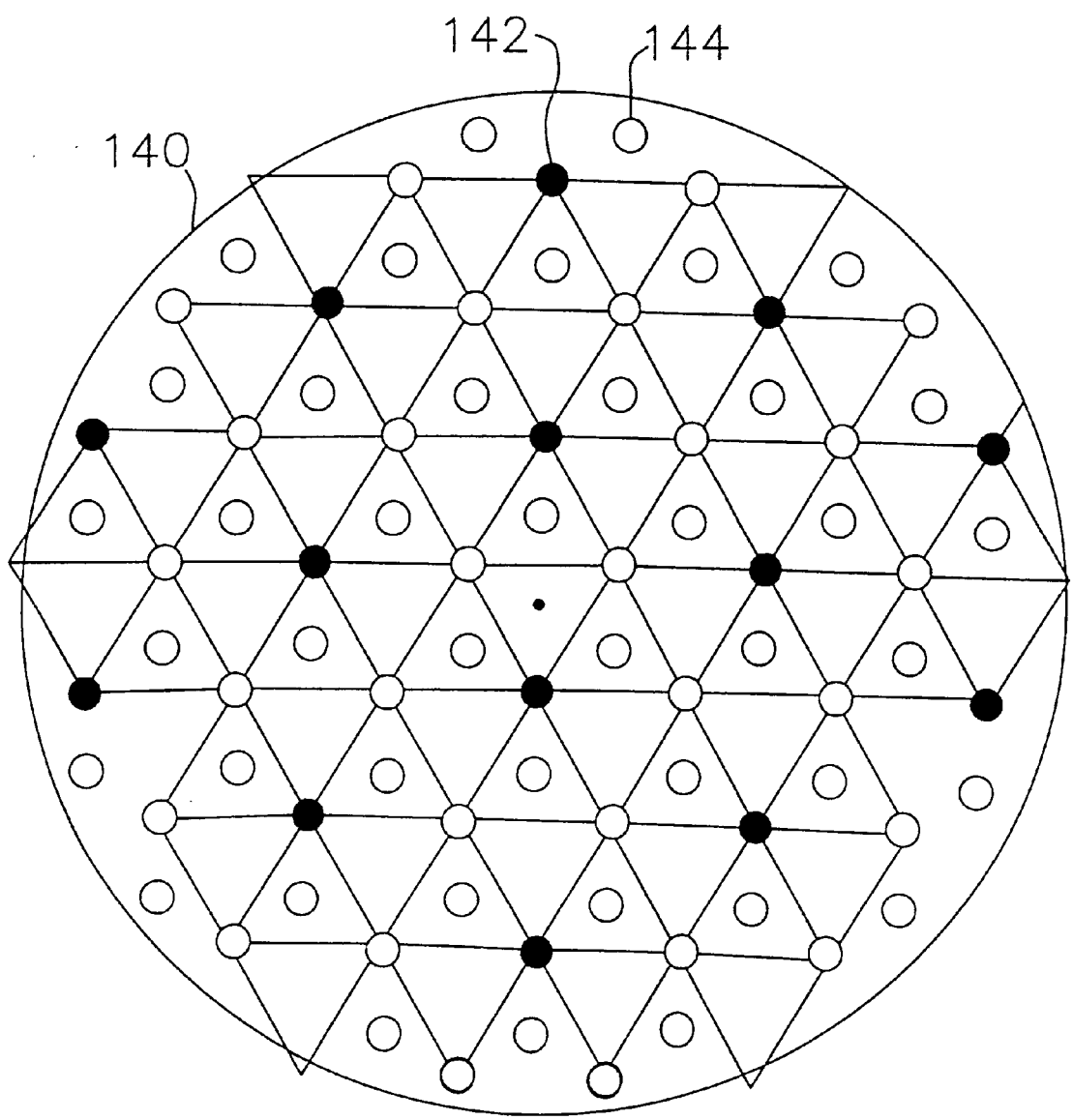
FIG. 5 is yet another diagram showing the pattern of interrogation points of a device embodying the invention.

A third arrangement for the optical fibers of a device shown in FIG. 1 is depicted in FIG. 5. In this embodiment, the optical fibers are again arranged according to a hexagonal honeycomb pattern. However, far fewer optical. fibers are used, in this embodiment. This third embodiment is intended for use in a measurement process that calls for six measurement cycles. The inner core of the device would be rotated 60° between each measurement cycle. Over the course of the six measurement cycles, the device would ultimately interrogate all the black circled 142 and hollow circled 144 interrogation positions shown in FIG. 15. This embodiment allows for even greater separation distances between interrogation positions (to reduce or substantially eliminate cross-talk) while still achieving excellent measurement resolution. In addition, far fewer optical fibers and corresponding detectors would be required to achieve a given measurement resolution.

Experimental studies were conducted by the applicants to determine the spacing between interrogation positions that is needed to substantially eliminate cross-talk. The studies were conducted using a pair of optical fibers at each interrogation position, wherein one fiber in each pair provides excitation light, and the other fiber in each pair is used to detect light. The excitation optical fibers had a diameter of approximately 200 mm, and the detection fibers had a diameter of approximately 100 mm. Measurements were made on optical reference standards, and tissue. Under these conditions, it was necessary to space the interrogation positions approximately 3 mm apart to substantially eliminate cross-talk. Thus, if an instrument were not designed as described above, so that the inner core can rotate the interrogation positions to different locations on the target tissue, the device would only be capable of achieving a resolution of approximately 3 mm.

Figure 6:
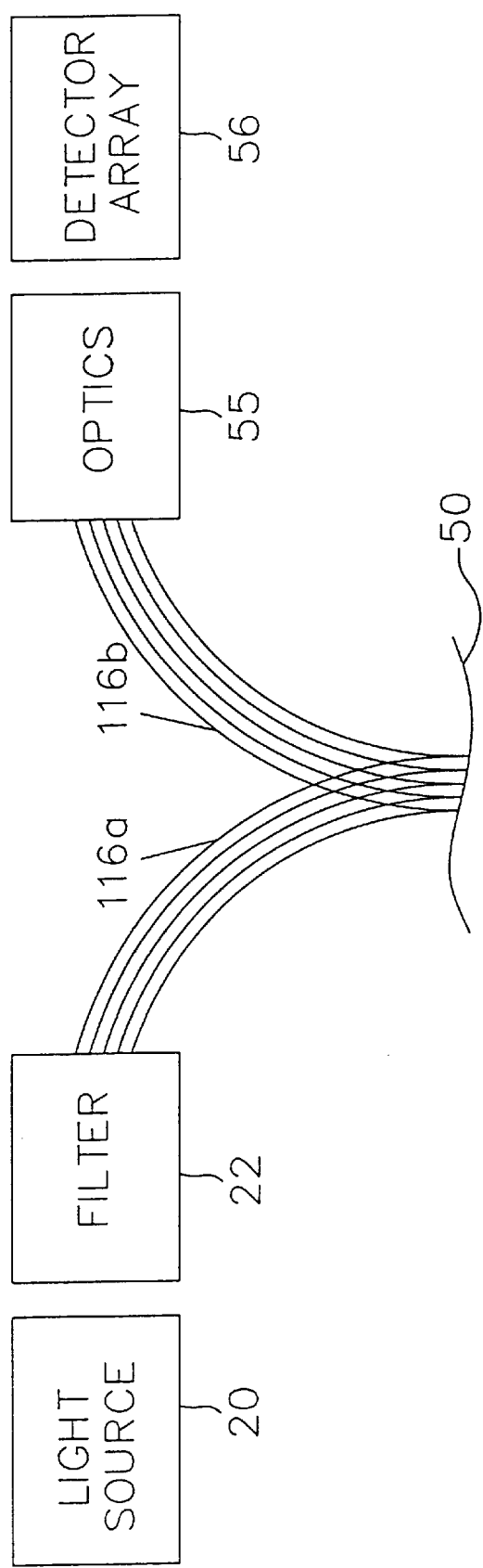
FIG. 6 is a block diagram of a device embodying the invention.

To determine the locations of diseased areas within a target tissue it is necessary to take measurements at a plurality of different locations in the target tissue spaced in at least two dimensions. Each measurement may require multiple excitation wavelengths, and detection of multiple wavelengths of scattered or generated light. Thus, the measurements involve three measurement dimensions, two dimensions for the area of the target tissue, and a third dimension comprising the spectral information. A device capable of conducting measurements in these three dimensions is shown in FIG. 6.

The instrument includes a light source 20, and a filter assembly 22. A plurality of excitation optical fibers 116a lead from the filter assembly 22 to the target tissue 50. A plurality of detection fibers 116b lead away from the target tissue 50. The excitation optical fibers 116a and the detection optical fibers 116b are arranged in pairs as described above.

The light source 20 and filter assembly 22 allow specific wavelengths of light to be used to illuminate the target tissue 50 via the excitation optical fibers 116a. The filter assembly 22 could be a single band pass optical filter, or multiple optical filters that can be selectively placed between the light source 20 and the excitation optical fibers 116a. In other embodiments, the filter assembly 22 could comprise an electrically switchable color filter which can selectively pass/block specific wavelength bands of light in response to electrical control signals. Alternatively, the light source 20 and filter assembly 22 could be replaced with a wavelength tunable light source. In yet other alternate embodiments, a plurality of light sources, such as lasers, could be used to selectively output specific wavelengths or wavelength bands of excitation light.

The detection fibers lead to an optical system 55. The light from the detection fibers 116b passes through the optical system and into a detector array 56. The detector array may comprise a plurality of photosensitive detectors, or one or more spectrophotometers. The detector array 56 is preferably able to obtain measurement results for each of the detection fibers 116b simultaneously.

The optical system 55 can include a plurality of optical filters that allow the detector array to determine the intensity of light at certain predetermined wavelengths or wavelength bands. In a preferred embodiment, the detector array would be a two dimensional array of photosensitive detectors, such as a charge coupled device (CCD). The optical system 55 would comprise a spectrograph that is configured to separate the light from each detection optical fiber 116b into a plurality of different wavelengths, and to focus the different wavelengths across several pixels on the CCD. Thus, a group of pixels on the CCD would correspond to a single detection fiber. The intensities of the different wavelengths of light carried by a single detection fiber 116b could be determined based on the outputs of a plurality of individual pixels of the CCD. The greater the output of a particular pixel, the greater the intensity at a particular wavelength or wavelength band.

According to another embodiment of the invention a device may be configured so that a portion of a plurality of optical fibers of a fiber optic probe are telescopically mounted. An example of such a periscoping fiber optic probe according to the invention is shown in FIG. 7.

Figure 7:
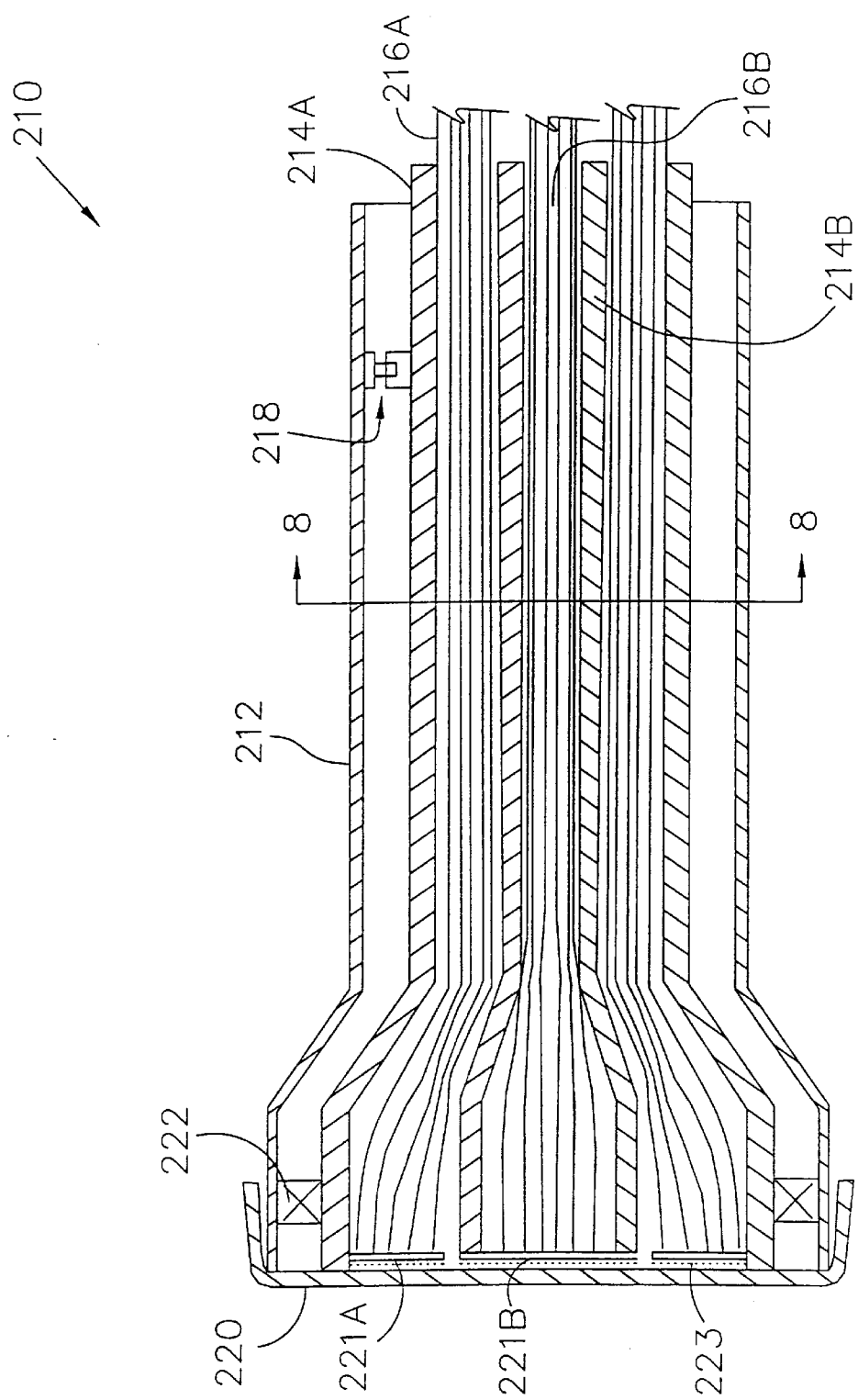
FIG. 7 is a cross-sectional view of a fiber optic probe according to another embodiment of the invention.

As shown in FIG. 7, the instrument 210 includes a cylindrical outer housing 212. A cylindrical rotating inner core 214A is buntced in the outer housing 212. A bundle of optical fibers 216A are located inside the rotating inner core 214A. A cylindrical periscoping inner core 214B is mounted within the rotating inner core 214A. The periscoping inner core 214B is mounted so that it can move axially with respect to the rotating inner core 214A. Preferably, the periscoping inner core 214B would rotate with the rotating inner core 214A.

The optical fibers 216A, 216B pass down the length of the inner cores 214A, 214B, respectively, and are arranged in a specific pattern at the end adjacent an end cap 220 of the outer housing 212. The end of the rotating inner core 214A is mounted within the outer housing with a rotating bearing 222. The end cap 220 is flexible and at least partially transparent or transmissive so that electromagnetic radiation can pass from the optical fibers, through the end cap 220, to illuminate a target tissue adjacent the end cap 220. Light scattered from or generated by the target tissue would then pass back through the end cap 220 and back down the optical fibers 216A, 216B.

Figure 8A:
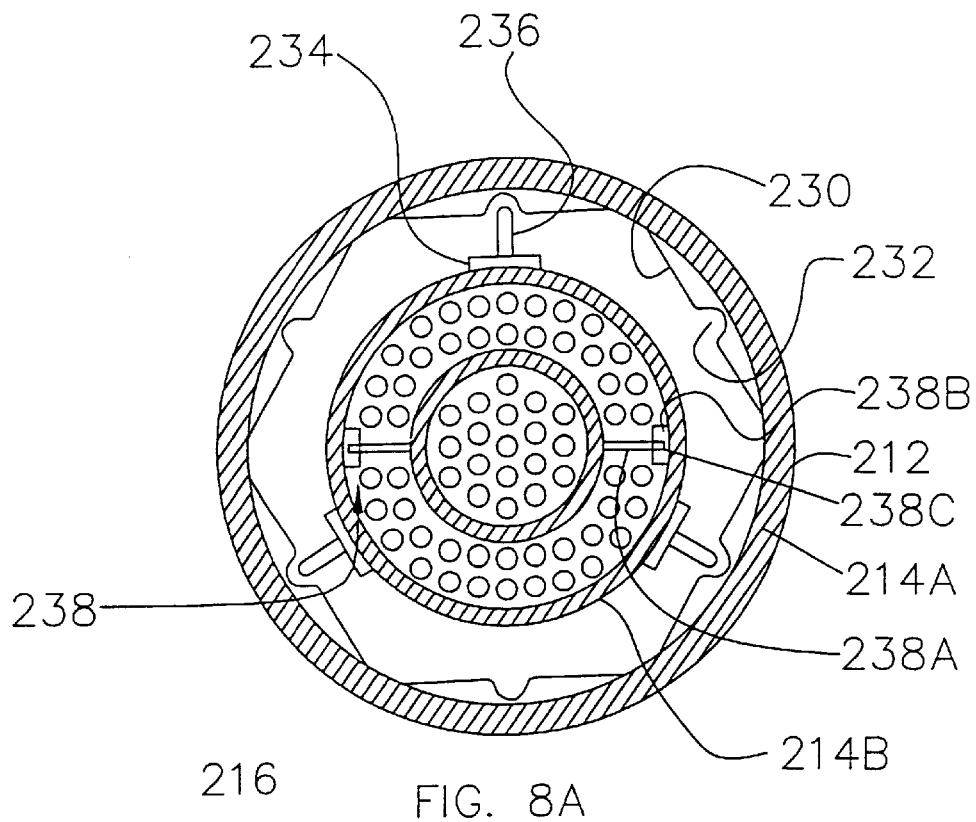
FIG. 8A is a cross-sectional view of the device of FIG. 7 taken along section line 8—8.
Figure 8B:
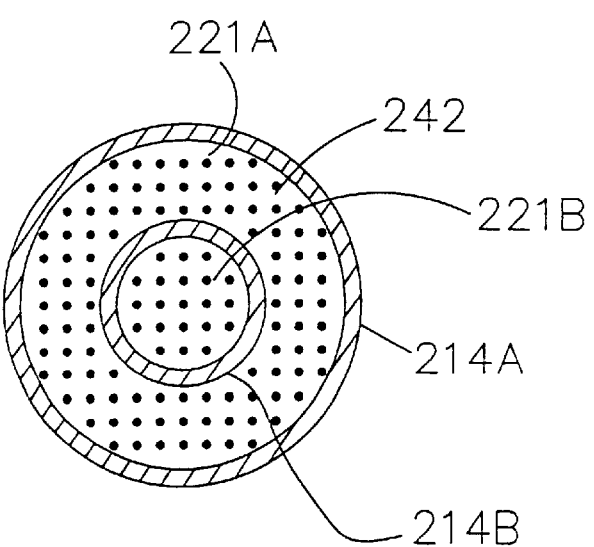
FIG. 8B is a diagram of the face of the fiber optic probe of FIG. 7.
Figure 9:
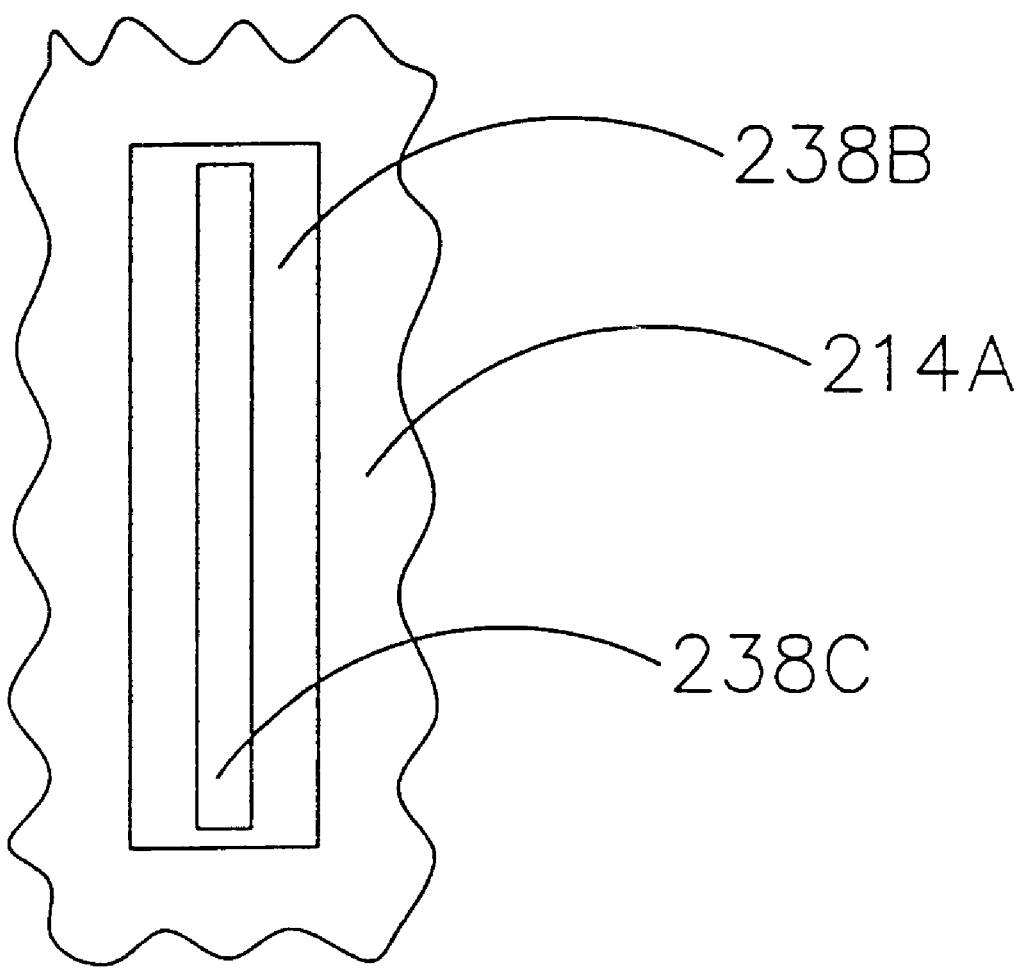
FIG. 9 is a front view of a stopper of a slide mechanism according to the invention.

A cross-sectional view of the device of FIG. 7, taken along section line 8—8, is shown in FIG. 8A. As shown in FIG. 8A, the periscoping inner core 214B is mounted inside the rotating inner core 214A by a slide mechanism which allows the periscoping inner core 214B to slide axially with respect to the rotating inner core 214A but rotate with the rotating inner core 214A when it rotates. As shown in FIGS. 8A and 8B, the mechanism is comprised of fingers 238A, which fit into grooves 238C of stoppers 238B. As shown in FIG. 9, the groove 238C extends along most of the length of the stopper 238B. The stopper 238B is mounted on an inner wall of the rotating inner core 214A. The structure allows the periscoping inner core 214B to slide axially with respect to the rotating inner core 214A. However, when the rotating inner core 214A is rotated, the periscoping inner core 214B rotates along with it. The axial movement of the periscoping inner core 214B is delimited by the length of the groove 238C.

Of course, other structures could be used in place of the one shown in FIGS. 8A, 8B and 9. The other structures would also allow one portion of the device to move axially with respect to another part so that an end face of the probe can conform to non-uniform surface areas of a target material. In the other structures, the axially slidable portion may or may not be rotatable with the stationary part. Also, the mechanism may be constructed so that the axially slidable portion can rotate, and the stationary part does not.

The rotating inner core 214A is supported within the outer housing 212 by the detent mechanism 218. In this embodiment, the detent mechanism includes three mounts 234 with spring loaded fingers 236 that are biased away from the rotating inner core 214A. The detent mechanism also includes 6 stops 230, each of which has a central depression 232. The spring loaded fingers 236 are configured to engage the central depressions 232 of the stops 230 to cause the rotating inner core 214A to come to rest at predetermined angular rotational positions. As previously discussed, the periscoping inner core 214B rotates with the rotating inner core 214A.

As shown in FIG. 7, the ends of the optical fibers are preferably positioned on or adjacent to circular end plates 221A, 221B that hold the optical fibers in a predetermined pattern, as shown in FIG. 8B. The circular end plate 221A preferably includes a centrally located opening for the periscoping inner core 214B. The circular end plates 221A, 221B are preferably rigidly attached to ends of the rotating inner core 214A and periscoping inner core 214B, respectively. In addition, an index matching agent 223 may be located between the end plates 221A, 221B and the end cap 220 on the outer housing 212.

The black circles 242 in FIG. 8B represent the locations of the optical fibers upon initial positioning of the fiber optic probe adjacent a target material. The optical fibers will move to new positions when the rotating inner core 214A and periscoping inner core 214B are rotated, similar to the depiction shown in FIG. 13, in which the hollow circles represent the positions that the optical fibers will move to upon rotation.

In some embodiments of,the device, a single optical fiber will be located at each of the positions shown by the black circles 242 in FIG. 8B. In this instance, excitation light would travel down the fiber and be emitted at each interrogation position indicated by a black circle 242. Light scattered from or produced by the target tissue would travel back up the same fibers to a detector or detector array. In alternate embodiments, a pair of optical fibers could be located at each interrogation position, where one optical fiber of each pair would conduct excitation light to the target tissue, and the second optical fiber of each pair would conduct light scattered from or generated by the target tissue to a detector.

In still other alternative embodiments, multiple fibers for carrying excitation light and/or multiple fibers for carrying light scattered from or generated by the target tissue could be located at each interrogation position indicated by a black circle 242.

To use an instrument as shown in FIG. 7, the instrument would first be positioned so that the end cap 220 is adjacent the target tissue. The end cap 220 may be in contact with the target tissue, or it might be spaced from the surface of the target tissue. The periscoping inner core 214B would then be axially extended to conform the probe face to the surface of a target tissue, such as, for example, the cervix of a patient. Also, an index matching material may be interposed between the end cap 220 and the target tissue. Then, the optical fibers would be used during a first measurement cycle to simultaneously measure tissue characteristics at each of the interrogation positions shown in FIG. 8B having a black circle 242. The tissue characteristics could be measured using any of the measurement techniques previously discussed. Then, the rotating inner core 214A, along with the periscoping inner core 214B, would be rotated within the outer housing 212, and the optical fibers would be used during a second measurement cycle to simultaneously measure tissue characteristics at each of another set of interrogation positions. In some instances, the periscoping inner core 214B would be withdrawn before the assembly is rotated. Afer rotation, the periscoping inner core 214B would be extended back out so that the probe face conforms to the target tissue.

In particular embodiments of a device as shown in FIG. 7, the end plates 221A, 221B may have shapes that allow the face of the probe to better conform to a non-uniform target material. Some examples of suitable shapes are discussed below in conjunction with different embodiments of the invention.

Constructing an instrument as shown in FIGS. 7, 8A and 8B has several important advantages. First, constructing an instrument in this manner allows the instrument to interrogate many more points in the target tissue that would have been possible if the inner cores did not rotate. The ability to rotate the inner cores, and take additional series of measurements at different locations on the target tissue, essentially increase the resolution of the device. Further, because the periscoping inner core 214B is axially movable, the probe face can more readily conform to the surface of certain target tissue shapes. In particular, this design would allow the probe face to conform to the tissue surface of a cervix (which has a central depression) better than a simple planer probe face.

Thus, an instrument as shown in FIGS. 7, 8A and 8B helps to balance the competing design requirements of resolution, elimination of cross-talk, and a desire to make a plurality of measurements simultaneously at multiple interrogation locations across the surface of the target tissue. Further, as discussed above, by capturing a plurality of measurements at different locations across the surface of the target tissue, one is better able to detect the presence of diseased tissue by comparing the diseased areas to normal tissue which is measured at the same time.

As previously discussed, the end cap 220 is a transparent or transmissive optical window or barrier. This barrier serves several purposes including, but not limited to, serving as a sterilizable or single use interface for the protection of the patient; protecting instrument parts from the ingress of bodily fluids; providing a patient contact surface that is benign and free of material related hazards; shielding the patient from possible electrical discharge with metal parts used in the instrument; and providing an optical conduit between the device and patient tissue.

The end cap 220 should be flexible enough that it readily conforms to the shape of the tissue surface during measurement. The end cap 220 must also fit tightly over the surface of the probe face. The end cap 220 is preferably flexible and membrane-like with a low durometer (i.e., high stretchability) and high tear strength in order to prevent breakage. Further, the end cap 220 is preferably optically clear with a high transmission of wavelengths ranging from approximately 280 nm to approximately 700 nm. The end cap 220 should also be optically uniform across the entire window surface.

One presently preferred option for the end cap material is dimethyl silicone, with a preferred durometer of 20 (on shore A scale) and a tear strength of 100 lbs/in. However, other materials may also be appropriate.

Figure 10:
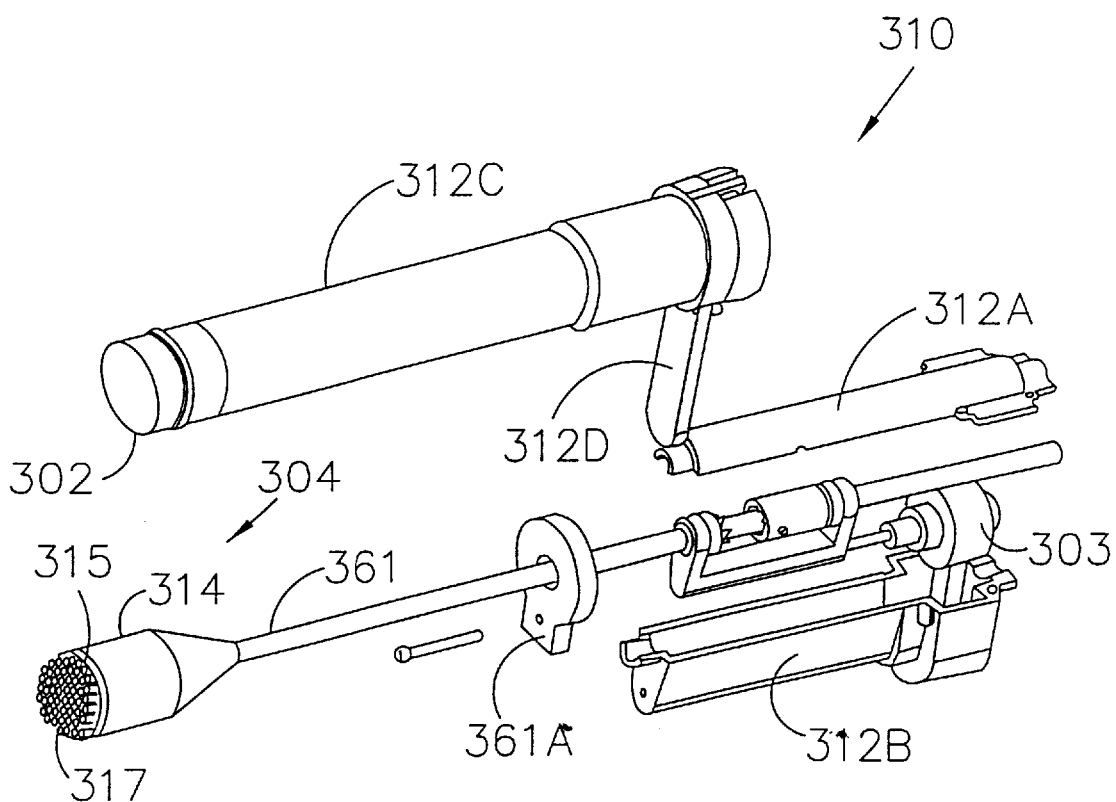
FIG. 10 is an exploded perspective of a fiber optic probe according to another embodiment of the invention.
Figure 11:
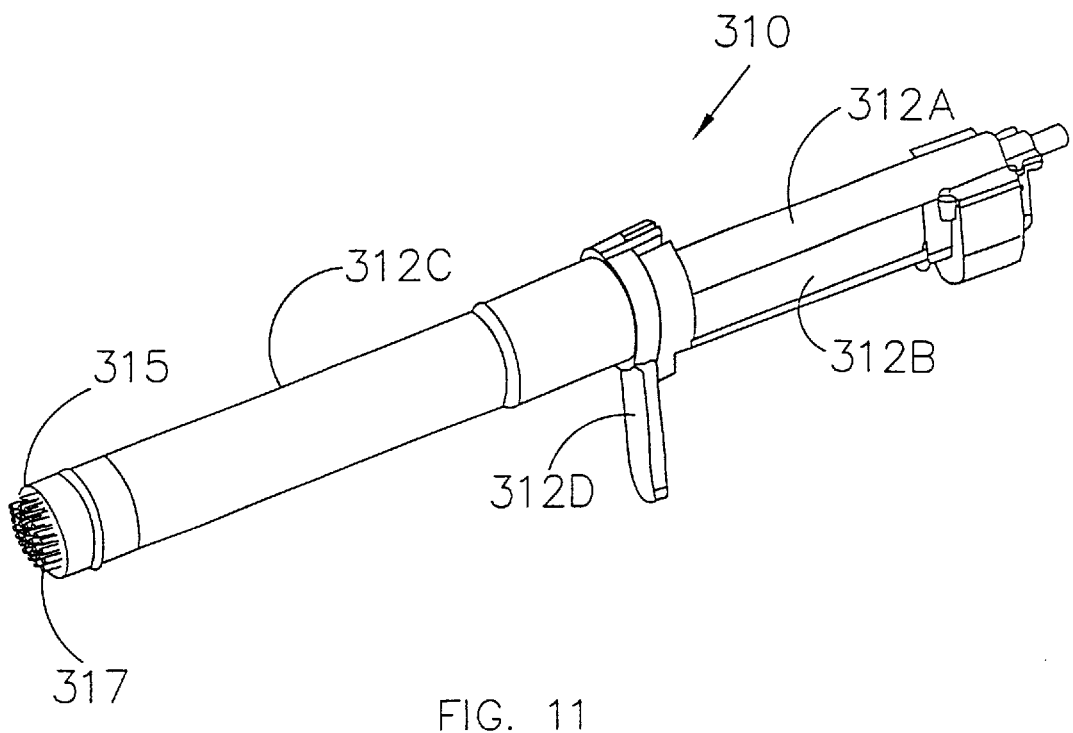
FIG. 11 is a perspective view of the device of FIG. 10 after assembly.

Another embodiment of the invention is shown in FIGS. 10 and 11. FIG. 10 is an exploded view of the device of FIG. 11.

The device 310 includes outer casing 312A, 312B, 312C, a mount/handle 312D, and a cover 302 for when the device is not in use. A probe head 304, including a rotatable inner core 314, a probe face 315 and a plurality of fiber optic probe elements 317, is mounted on a rotatable shaft 361. The rotatable shaft 361 is supported in a bearing 361A and is rotated by a movement mechanism 303.

The movement mechanism 303 could simply rotate the shaft 361 and probe face 315. In addition, the movement mechanism could also be configured to move the shaft 361 and probe face 313 axially within the casing 312C.

Each fiber optic probe element 317, or pin, is spring-loaded and is held within a corresponding cylindrical hole on the probe face 315. Each spring-loaded fiber optic probe element 317 is comprised of a hollow shaft 319, as shown in FIG. 16B. Each shaft 319 has an axially extending opening 319A for housing one or more optical fibers 316. A spring 318 can be located below the shaft 319, as shown in FIG. 16B, or the spring could surround a lower portion 319C of the shaft 319, as shown in FIG. 16A. Because the fiber optic probe elements 317 are each spring-loaded, they can collectively conform to a non-uniform surface area of a target material. Of course, many other options would be available to bias the fiber optic probe elements 317 away from the probe face 315.

As shown in FIG. 15, the probe face 315 is preferably covered with a flexible window or membrane 320, such as the flexible window or membrane previously discussed. The flexible window or membrane 320 must readily conform to the collective positions adopted by the fiber optic probe elements 317 during measurement, that is, the flexible window 320 surface must not hinder the free movement of the pins or substantially impair the "springiness" of the probe elements 317. Preferably, the flexible window 320 would fit tightly over each probe element 317 as to prevent air gaps from forming between the probe element 317 and the flexible window 320.

In operation, the probe face 315, with its flexible window covering 320, would be pressed against the target tissue to be examined. This would cause at least some of the fiber optic probe elements 317 to be depressed into the face 315 against the bias of the corresponding springs 318. In this manner, the flexible window 320 would conform to an uneven/non-planer surface area of the target tissue. Provided the flexible window 320 has sufficient flexibility, the flexible window 320 should remain in contact with the target tissue regardless of the contours of the target tissue.

Figure 12:
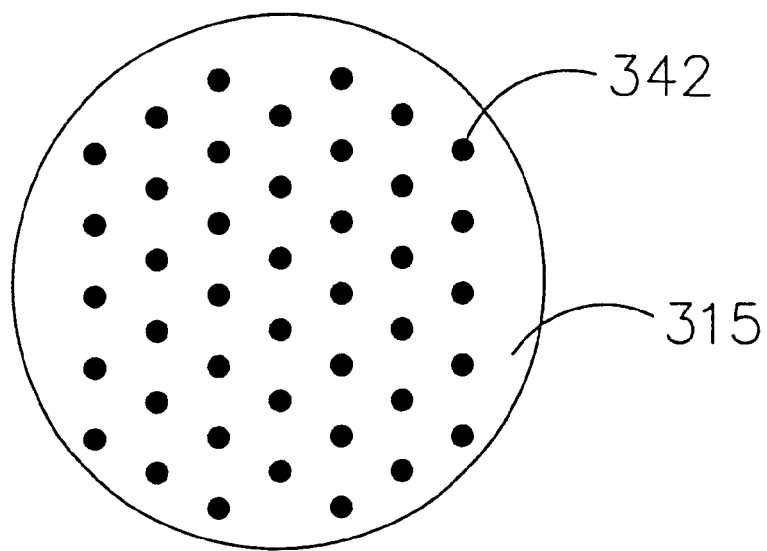
FIGS. 12 and 13 are schematic diagrams of the face of the fiber optic probe of FIG. 11 showing exemplary positions of the optic fibers.
Figure 13:
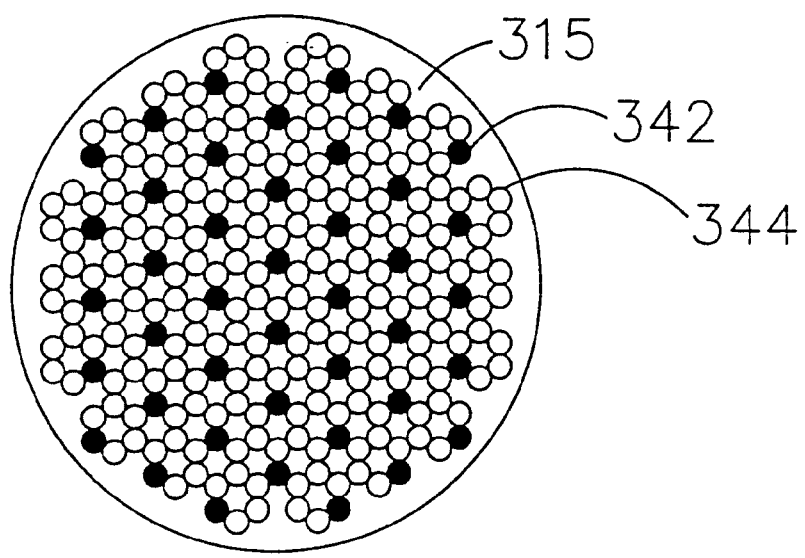

The fiber optic probe elements 317 are preferably positioned in a uniform geometric pattern over the probe face 313, as shown in FIG. 12. The arrangement of the fiber optic probe elements 317 is designed such that by rotating the probe face 315 through a 60° angle the fiber optic probe elements 317 interrogate an equispaced but different set of positions on the target material. By rotating the probe face 315 a total of five times (6 positions), 42 fiber optic elements 317 could be used to interrogate a total of 252 different locations on the target tissue. This scheme is illustrated in FIG. 13, where the dark circles 342 represent the original optic fiber probe elements arrangement and the open circles 344 represent the new positions occupied over successive rotations of the probe. In this manner, a large number of points on the tissue are interrogated. The spatial resolution is roughly multiplied 6 fold. Given an approximately 3.4 mm separation between each fiber or fiber pair on the face of the probe, the target material surface is sampled roughly every approximately 1 mm after the probe is rotated through 6 positions.

In the preferred embodiment shown in FIGS. 10 and 11, the rotation of the probe face 315 is motorized and automated in order to simplify the measurement procedure. Preferably, the probe face 315 is at least partially retracted into the outer casing 312C prior to rotation. This helps to prevent the fiber optic probe elements 317 from rubbing against the flexible sheath or window 320 during rotation. The rotation and retraction can be performed by, for example, a linear stepper motor. A suitable single 12V linear stepper motor is made by Haydon Switch and Instrument Inc., in Waterbury, Conn. as part no. Z26542-12-004, which combines linear actuation and rotation in a single motion. The stepper motor can be controlled using a driver controller, such as, for example, the driver controller made by API Controls in Amherst, N.J. as part no. DM 224-IO.

The sequence for measuring at each rotation position is as follows. The probe face 315 is first extended out of the casing 312C and is brought adjacent to or in contact with the inner surface of the flexible window 320. The probe end would then be brought into contact with the target tissue and the probe end would be pressed against the target tissue so that at least some of the fiber optic probe elements 317 are pushed into the probe face 315 against the springs. Spectral measurements are then made at each of the interrogation positions adjacent the fiber optic probe elements 317. Then the probe head is withdrawn into the casing 312, the probe head is rotated 60°, and the probe head is pushed back into position against the target tissue. This procedure is repeated, as necessary, to interrogate all desired locations on the target material.

The uterine cervix, for example, has a curved, donut shaped, surface with the endocervical canal located approximately in its center. The sloped area in the center of the cervix leading to the canal would not be accessible to a probe having a planar end face. The Squamo-Columar (SC) junction, the area where most disease is found, occurs in this "missed" area. The remaining portions of the surface profile of the cervix varies in depth, slope and shape making a "one size fits all" contoured surface probe unsatisfactory. In addition there are other surface undulations that are patient specific. The patient may have had prior surgical removal of tissue (LEEP or cryosurgery) that would present a nonuniform surface of the cervix for measurement. Given these considerations, the novel approach to adapting the surface of the probe to any surface (within a certain range) was taken.

An added advantage of such an approach is that a calibrated and constant force pressing the fiber optic probe elements 317 against the tissue can be maintained by designing the device with appropriate spring characteristics.

Figure 14:
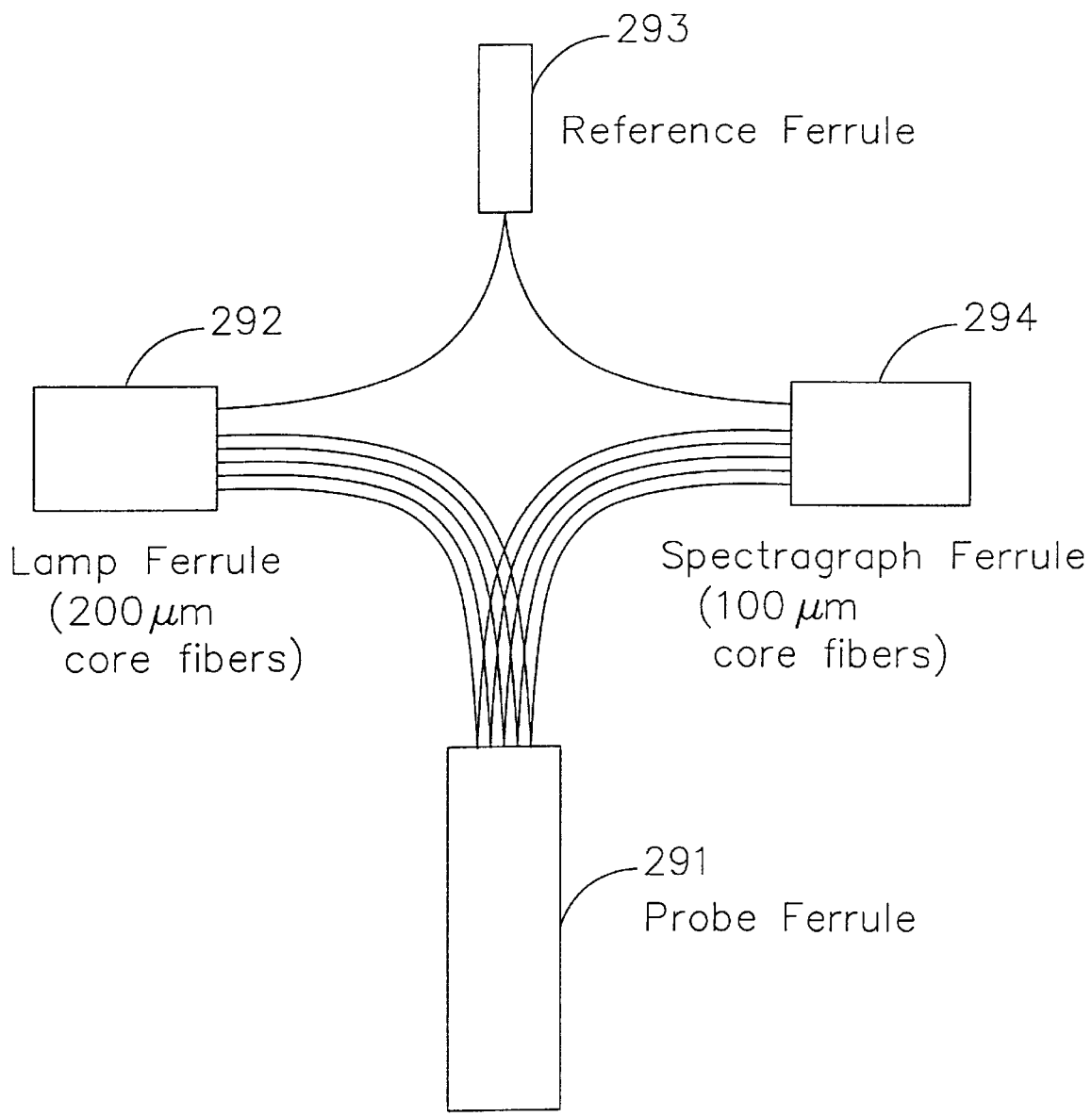
FIG. 14 shows the general layout of an entire fiber optic probe of FIG. 11 in block diagram form.

FIG. 14 shows the general layout of a fiber optic probe embodying the invention in block diagram form. The fiber optic probe includes a probe ferrule 291, a reference ferrule 293, a lamp ferrule 292 and a spectrograph ferrule 294. All of the collection optic fibers, plus an additional reference fiber, are aligned in a vertical column and placed at the entrance slit of the spectrograph ferrule 294. All of the excitation fibers from the probe and a reference fiber are also arranged in a random tight circle at the lamp ferrule 292.

When a measurement is taken using the probe shown in FIG. 14, excitation light from the lamp ferrule 292 would illuminate a portion of the reference ferrule 293. Light backscattered or reflected from the reference ferrule would be collected by a reference fiber that then travels through the spectrographic ferrule 294. A detector element would be positioned within the spectrograph ferrule 294 to detect the light scattered or reflected from the reference ferrule. A signal from this detector would then be used to calibrate or reference readings coming from the probe ferrule 291. Excitation light would also be sent from the lamp ferrule 291 to the probe ferrule 291. The probe ferrule 291 would be positioned adjacent to the target tissue, and the excitation light would be coupled to the target tissue at the interrogation end of the probe ferrule. Scattered or reflected excitation light, or fluorescent light produced in response to the excitation light, would then be coupled back into the probe ferrule 291. This response light would then be conveyed by optical fibers over to the spectrograph ferrule 294. Detectors within the spectrograph ferrule 294 would be used to detect characteristics of the light coming from the target tissue.

Figure 17:
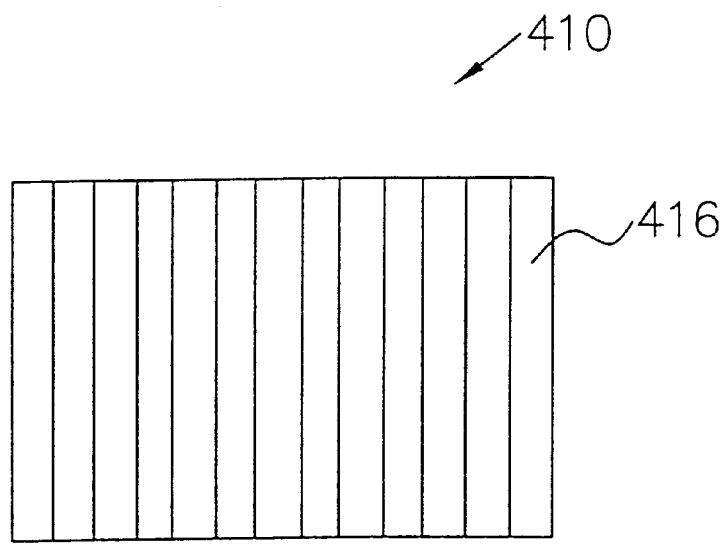
FIG. 17 is a diagram of a fused fiber optic probe head.

Another embodiment of the invention makes use of a fused coherent bundle of fibers, also known as a cane, as the probe head. As shown in FIG. 17, the probe head 410 is formed of a chunk of glass having a plurality of light conducting passageways 416.

To create a probe head like the one shown in FIG. 17, a chunk of glass is doped to form two layers, a core surrounded by a cladding, thus forming the basics of an optical passageway 416. The chunk of glass is then heated and drawn out lengthwise, then folded over to double the material, and hence the number of optical passageways 416. This process is repeated multiple times, and each time the material is drawn and folded over, the number of optical passageways 416 is doubled and the individual passageways become thinner. For example, there can be 10,000 optical passageways in an approximately 3.4 mm diameter cane. This process is repeated until the cane or probe head contains the desired number of optical passageways. When the material is folded over onto itself, because of the temperature of the material, the individual halves fuse together.

Additionally, as the material is drawn out, one end can be drawn away to form a tapered cane, where one end is thinner than the other. Such a cane could be used in a probe head to magnify or de-magnify an image of an object. Further, the cane can be twisted to produce a probe head that inverts an image of an object.

Normally, the end of the cane is cut off perpendicular to the central axis of the cane, which provides a flat image of an object. Some canes may have shaped ends, which can act as a lens, to produce desired optical properties.

The present invention comprises using a cane as described above as a probe head, and shaping the end of the probe head, that is, the distal end of the probe head, to compliment the surface of the target material. More particularly, the invention proposes making a non-flat image plane for purposes of analyzing a non-uniform surface area of the target material.

Figure 18:
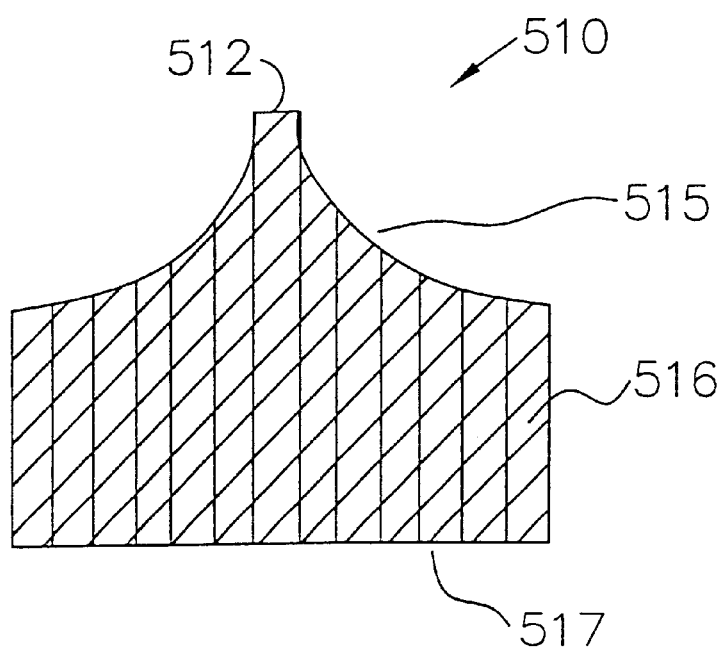
FIG. 18 is a diagram of a shaped fused fiber optic probe head according to the invention.

For example, the end of the fused cane head could be ground and polished using a diamond machine to shape the end according to the geometry of the target material to be interrogated. The end of the cane would be shaped to conform to the geometry of the target material to be probed. One embodiment of a cane probe head embodying the invention is shown in FIG. 18. FIG. 18 is cross-sectional view showing a circular probe head 510 which has been cut across the center. The probe head 510 would be generally circular, and have a conical shape which rises to a point 512 at the center. A plurality of optical passageways 516 similar to the optical fibers, would run from the top to the bottom of the probe head 510. The conical shaped surface 515 of the probe head 510 would be designed to contact a target tissue area to be interrogated. The circular and conical shaped probe head 510 shown in FIG. 18 would be suitable for interrogating the cervix of a patient.

Light entering the probe head 510 at the shaped upper surface 515 would travel down the length of the optical passageways 516 to bottom surface 517. The flat bottom surface 517 could be interfaced to a detector or imaging device. Alternatively, the bottom surface 517 could be interfaced to another set of flexible optic fibers that lead to a detector or imaging device.

A fused optical fiber bundle, or cane, could be used as a low cost way to obtain a shaped probe end which would be interfaced to remaining portions of a spectroscopic interrogation device. As a result, an interrogation device capable of analyzing scattered excitation light or fluorescent light generated by a target tissue could be configured to receive any of a plurality of detachable probe heads, formed as shown in FIG. 17, or with other shapes that can conform to non-uniform target materials. This would allow a user to select an appropriately shaped probe head which would best conform to the target tissue being interrogated.

Figure 19:
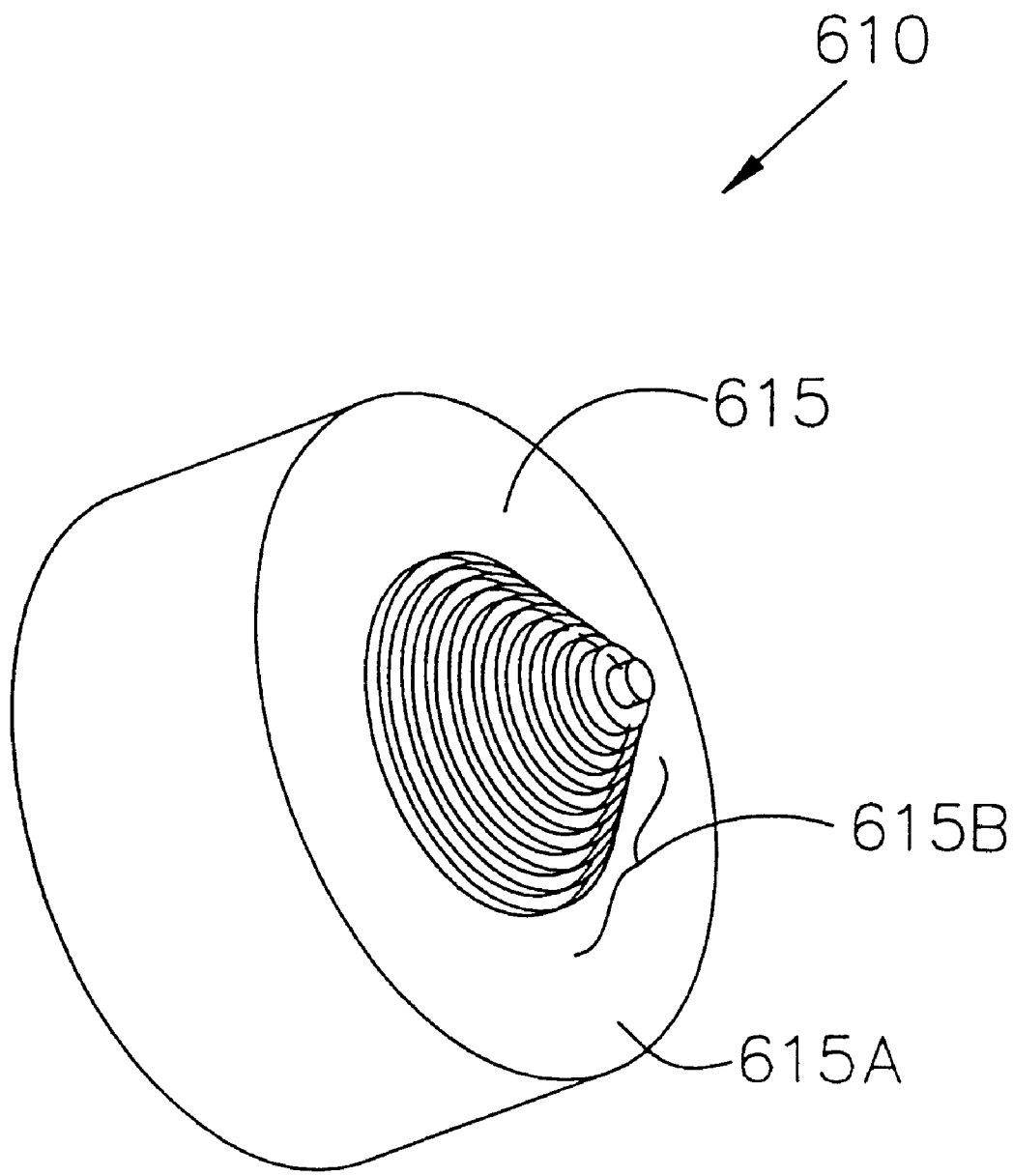
FIG. 19 is a perspective view of a fiber optic probe according to another embodiment of the invention.
Figure 20:
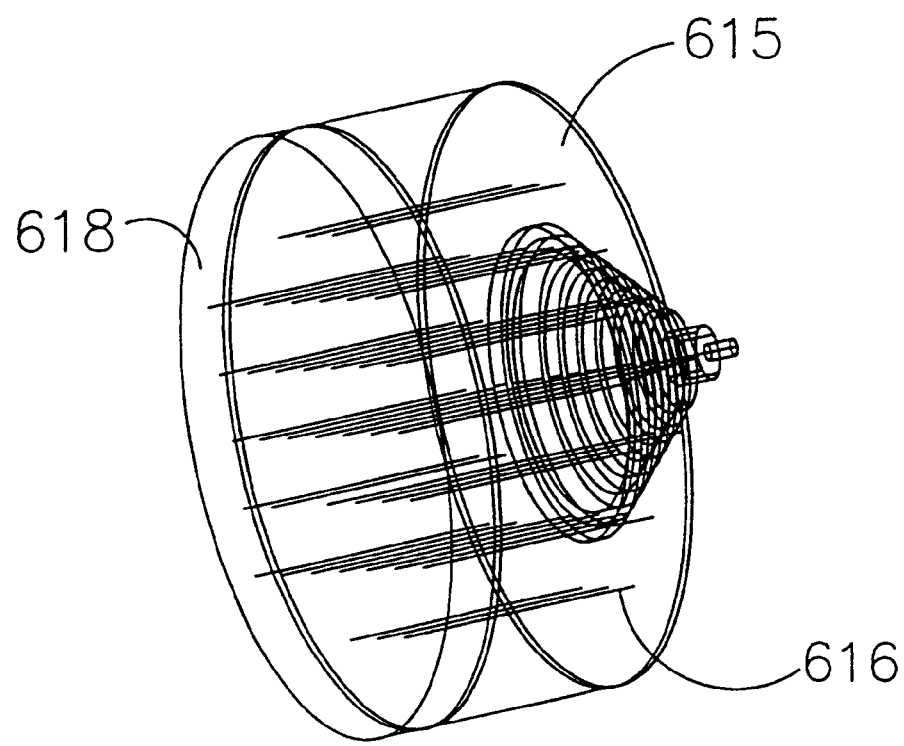
FIG. 20 is a schematic diagram showing exemplary positioning of the optic fibers of the device of FIG. 19.

Another probe end embodying the invention is shown in FIGS. 19–20. FIG. 19 shows a fiber optic probe end 610 having a face 615 shaped to conform to a non-uniform contour of a target material. This particular configuration allows investigation of the OS and transitional zone of the cervix. A probe end embodying the invention could also have other configurations specifically designed to conform to the contour of other target tissue areas.

In the particular configuration shown in FIG. 19, for interrogation of the cervix, the outer flat portion 615A is utilized for interrogating the ectocervix while the inner stepped portion 615B is used for interrogating the OS and endocervical canal. The inner stepped portion 615B can be fixed with respect to the outer flat portions 615A, or the inner stepped portion 615B can be designed to slide axially with respect to the outer flat portions 615A. This would provide flexibility in positioning of the inner portion 615B within the depths of the cervix and would allow the device to conform to the particular patient's anatomy.

FIG. 20 shows that optic fibers 616 would run from the top surfaces of the probe head 610 down to a rear surface 618. The optical fibers 616 could then run from the rear surface 618 of the probe head 610 onto a detector unit. Alternatively, the optical fibers 616 within the probe head 610. could terminate at the rear surface 618. In this instance, additional optical fibers could couple to the rear surface 618 so that the optical fibers within the probe heads 610 communicate with an additional set of flexible optical fibers which lead to a detection device. This type of an arrangement could allow a plurality of different probe heads 610 having, different shapes, to be coupled to the same basic interrogation device.

Figure 21:
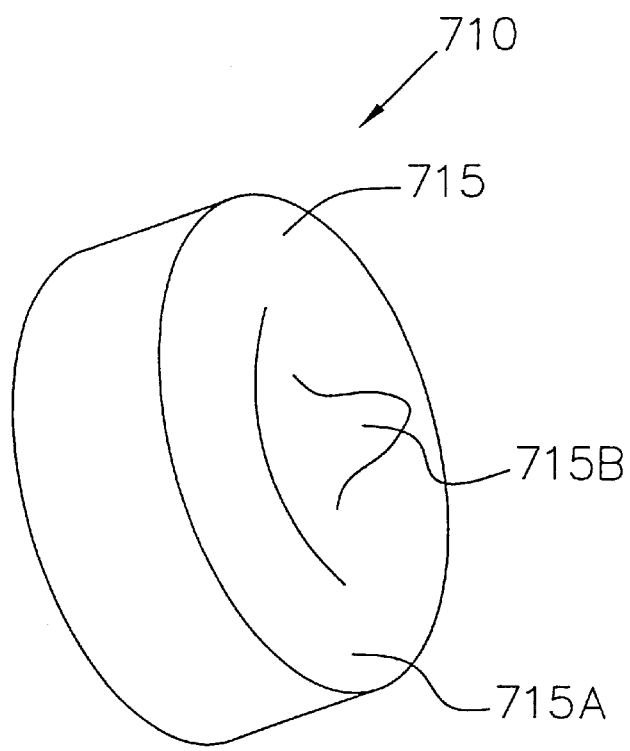
FIG. 21 is a perspective view of a fiber optic probe according to another embodiment of the invention.
Figure 23:
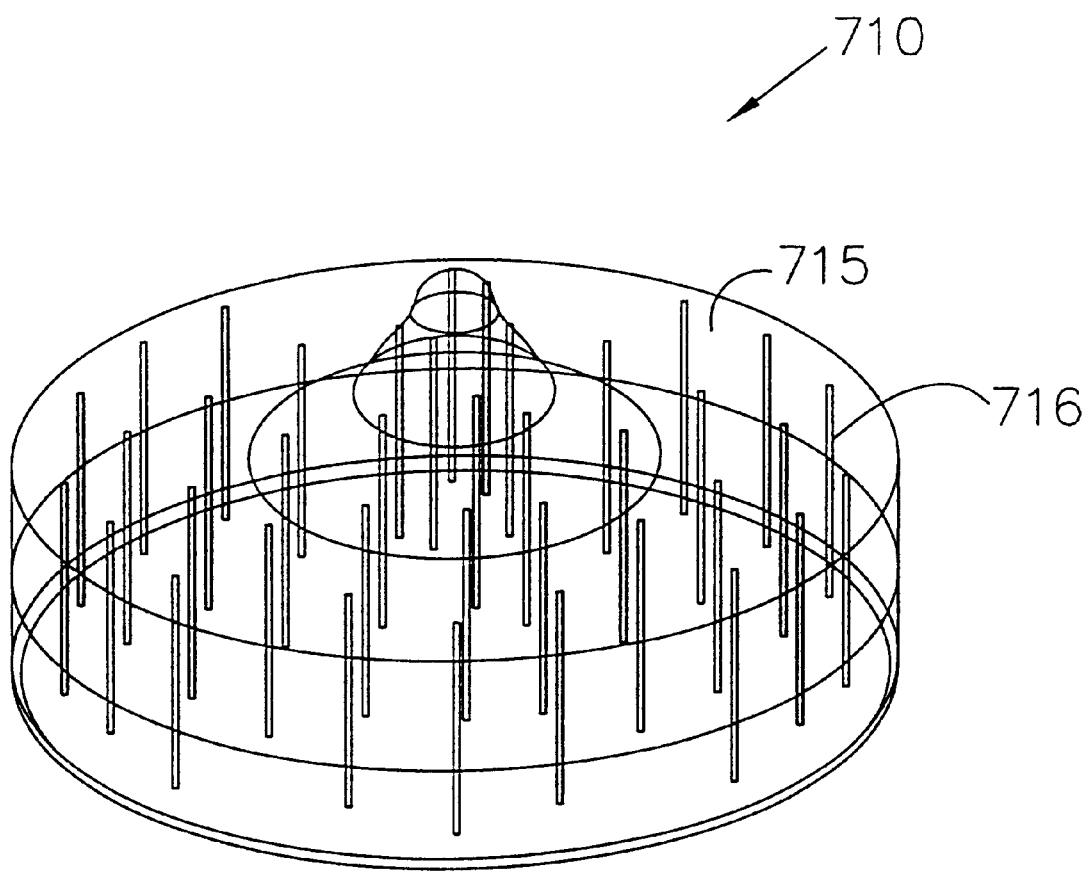
FIG. 23 is a schematic diagram showing exemplary positioning of the optic fibers of the device of FIG. 21.
Figure 24:
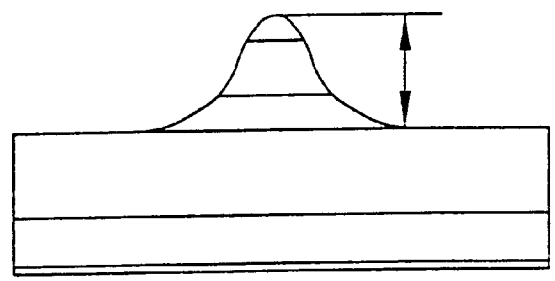
FIG. 24 is a side view of the device of FIG. 21.
Figure 25:
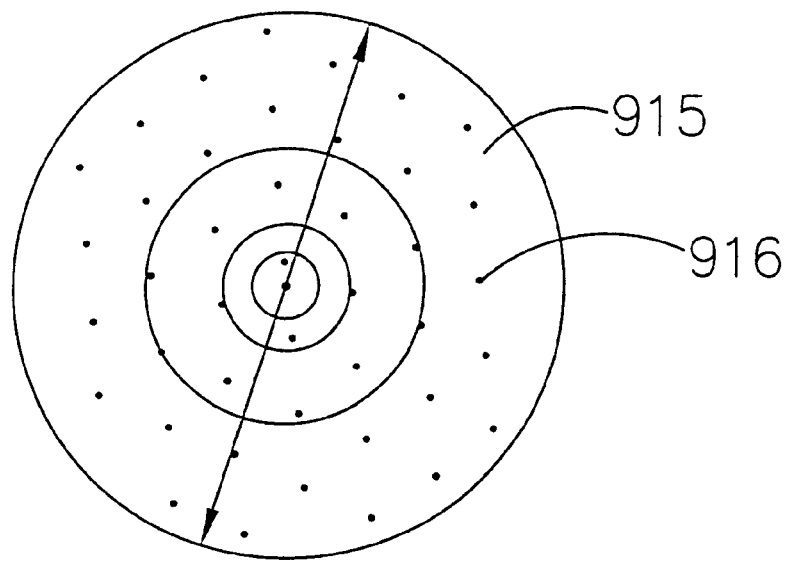
FIG. 25 is a front view of the device of FIG. 21.

FIG. 21 shows an additional configuration for a shaped probe head. The shaped probe head 710 of FIG. 21 has a flat portion that extends into a central conical portion 715B having a rounded tip. FIG. 23 provides a perspective view of this type of probe head. FIG. 23 shows an example of how optic fibers 716 can be positioned with respect to the face 715 of the shaped probe 710. FIG. 24 is a side view of the shaped probe 710 of FIG. 21. FIG. 25 is a top view of the shaped probe 710 of FIG. 21.

The shaped probe head 710 of FIG. 21 would be suitable for interrogating the surface of a cervix, since the probe head 710 allows the cervix/OS to conform to the surface of the probe head 710. A protective flexible disposable membrane can also be formed to fit the profile of the probe face.

Figure 22:
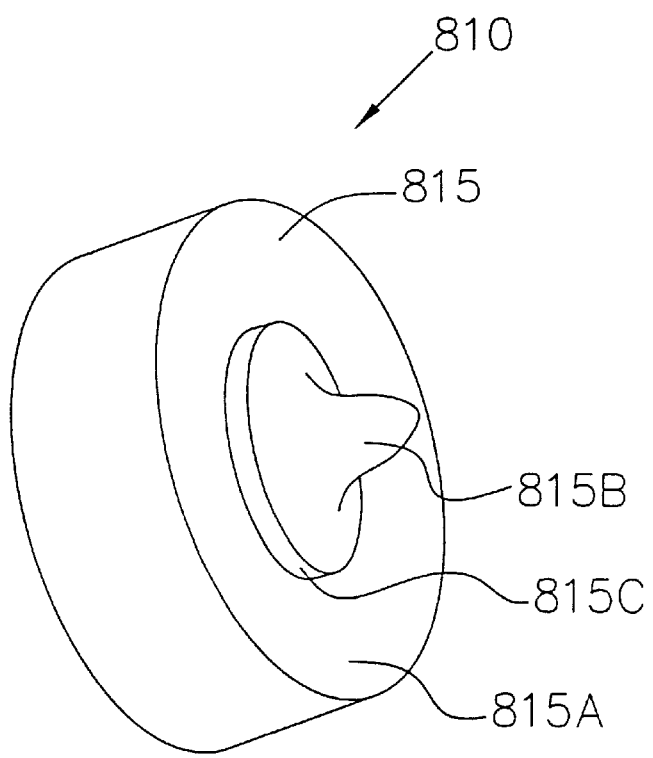
FIG. 22 is a perspective view of another fiber optic probe according to another embodiment of the invention.
Figure 26:
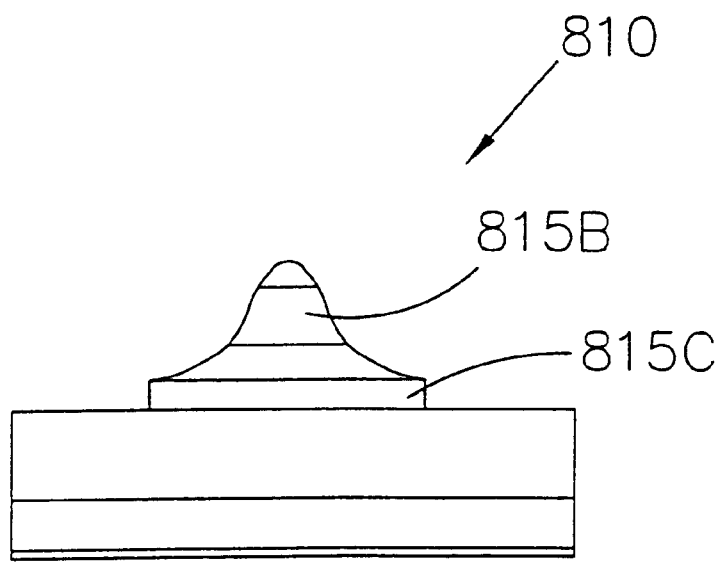
FIG. 26 is a side view of the device of FIG. 22.

A different shaped probe head 810, shown in FIG. 22, has a flat portion 815A, a stepped portion 815C and a central conical portion 815B with a rounded tip. FIG. 26 is a side view of the shaped probe of FIG. 22. The outer flat portion 815A of the shaped probe of FIG. 22 is designed to be used for interrogating the ectocervix, while the central conical portion 815B and stepped portion 815(C are used for interrogating the OS and endocervical canal. The central conical portion 815B and stepped portion 815C can be fixed with respect to the outer flat portion 815A, or they can slide axially with respect to the outer flat portion 815A. Allowing the central conical portion 815B and the stepped portion 815C to slide would provide flexibility in positioning of the inner portions 815B, 815C within the depths of the cervix and would allow the device to conform to the particular patient's anatomy.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method of detecting characteristics of a target material, comprising the steps of:

positioning a probe head having a plurality of interrogation devices adjacent a first plurality of interrogation positions on a non-uniform surface area of a target material so that the plurality of interrogation devices conform to the non-uniform surface area; and detecting optical characteristics of the target material at the first plurality of interrogation positions with the plurality of interrogation devices, wherein a portion of the plurality of interrogation devices are positioned on a first probe face, wherein a portion of the plurality of interrogation devices are positioned on a second probe face, wherein the second probe face is axially slidable with respect to the first probe face, and wherein the positioning step comprises moving the second probe face relative to the first probe face so that the plurality of interrogation devices conform to the non-uniform surface area of the target material.

2. The method of claim 1, wherein optical characteristics of the target material are detected at the first plurality of interrogation positions with the plurality of interrogation through an optical system coupled to the interrogation devices.

3. The method of claim 1, wherein the target tissue comprises biological target tissue.

4. A method of detecting characteristics of a target tissue, comprising the steps of:

positioning a probe head having a plurality of interrogation devices adjacent a first plurality of interrogation positions on a non-uniform surface area of a target tissue so that the plurality of interrogation devices conform to the non-uniform surface area; and detecting optical characteristics of the target tissue at the first plurality of interrogation positions with the plurality of interrogation devices, wherein a portion of the plurality of interrogation devices are positioned on a first probe face, wherein a portion of the plurality of interrogation devices are positioned on a second probe face, wherein the second probe face is axially slidable with respect to the first probe face, and wherein the positioning step comprises moving the second probe face relative to the first probe face so that the plurality of interrogation devices conform to the non-uniform surface area of the target tissue.

* * * * *